(12) United States Patent
Bucala et al.

(10) Patent No.: US 9,308,255 B2
(45) Date of Patent: Apr. 12, 2016

(54) METHODS OF ADMINISTERING D-DOPACHROME TAUTOMERASE (D-DT) TO TREAT ISCHEMIA-REPERFUSION INJURY

(75) Inventors: Richard J. Bucala, Cos Cob, CT (US); Lawrence H. Young, Woodbridge, CT (US)

(73) Assignee: Yale University, New Haven, CT (US)

( * ) Notice: Subject to any disclaimer, the term of this patent is extended or adjusted under 35 U.S.C. 154(b) by 149 days.

(21) Appl. No.: 13/989,182

(22) PCT Filed: Nov. 23, 2011

(86) PCT No.: PCT/US2011/062062
§ 371 (c)(1),
(2), (4) Date: Oct. 7, 2013

(87) PCT Pub. No.: WO2012/071525
PCT Pub. Date: May 31, 2012

(65) Prior Publication Data
US 2014/0030266 A1    Jan. 30, 2014

Related U.S. Application Data

(60) Provisional application No. 61/416,904, filed on Nov. 24, 2010.

(51) Int. Cl.
| | | |
|---|---|---|
| A61K 38/17 | (2006.01) | |
| A61K 39/395 | (2006.01) | |
| C07K 16/24 | (2006.01) | |
| C12Q 1/68 | (2006.01) | |
| A61K 31/713 | (2006.01) | |
| A61K 38/02 | (2006.01) | |
| G01N 33/68 | (2006.01) | |
| A61K 39/00 | (2006.01) | |

(52) U.S. Cl.
CPC ............ *A61K 39/3955* (2013.01); *A61K 31/713* (2013.01); *A61K 38/02* (2013.01); *C07K 16/24* (2013.01); *C12Q 1/6883* (2013.01); *G01N 33/6893* (2013.01); *A61K 2039/505* (2013.01); *C07K 2317/76* (2013.01); *C12Q 2600/158* (2013.01)

(58) Field of Classification Search
None
See application file for complete search history.

(56) References Cited

U.S. PATENT DOCUMENTS

| | | |
|---|---|---|
| 2008/0293583 A1 | 11/2008 | Khawaja et al. |
| 2009/0068656 A1 | 3/2009 | Beier et al. |
| 2010/0143379 A1 | 6/2010 | Bucala et al. |
| 2010/0196426 A1 | 8/2010 | Skog et al. |
| 2011/0183870 A1 | 7/2011 | Pan et al. |

FOREIGN PATENT DOCUMENTS

JP    02009178073    8/2009

OTHER PUBLICATIONS

Fingerle-Rowson et al., "A Tautomerase-Null Macrophage Migration-Inhibitory Factor (MIF) Gene Knock-In Mouse Model Reveals That Protein Interactions and Not Enzymatic Activity Mediate MIF-Dependent Growth Regulation," Mol Cell Biol, Apr. 2009, 29:1922-1932.
Shi et al., "CD44 Is the Signaling Component of the Macrophage Migration Inhibitory Factor-CD74 Receptor Complex," Immunity, Oct. 2006, 25:595-606.
Binsky, et al., "IL-8 secreted in a macrophage migration-inhibitory factor- and CD74-dependent manner regulates B cell chronic lymphocytic leukemia survival," Proc Natl Acad Sci USA, Aug. 2007, 104:13408-13413.
Leng et al., "MIF Signal Transduction Initiated by Binding to CD74," J Exp Med, Jun. 2003, 197:1467-1476.
Rosengren et al., "The Immunoregulatory Mediator Macrophage Migration Inhibitory Factor (MIF) Catalyzes a Tautomerization Reaction," Mol Med, Jan. 1996, 2:143-149.
Emonts, et al., Association between High Levels of Blood Macrophage Migration Inhibitory Factor, Inappropriate Adrenal Response, and Early Death in Patients with Severe Sepsis, Clin Infect Dis, May 2007, 44:1321-1328.
Hiyoshi et al., "D-Dopachrome tautomerase is a candidate for key proteins to protect the rat liver damaged by carbon tetrachloride," Toxicology, Sep. 2008, 255:6-14.
Zeng et al., "Protein Expression Changes in Human Monocytic THP-1 Cells Treated with Lipoteichoic Acid from Lactobacillus plantarum and *Staphylococcus aureus*," Mol Cells ePub May 2010, 29:585-594.
Odh et al., "Isolation of a New Tautomerase Monitored by the Conversion of D-Dopachrome to 5,6-Dihydroxyindole," Biochem Biophys Res Commun., Dec. 1993, 197:619-624.
Xin et al., "The MIF homologue D-dopachrome tautomerase promotes COX-2 expression through beta-catenin-dependent and -independent mechanisms," Mol. Cancer Res, Epub Nov. 2010, 8:1601-1609.
Coleman et al., "Cooperative regulation of non-small cell lung carcinoma angiogenic potential by macrophage migration inhibitory factor and its homolog, D-dopachrome tautomerase," J Immunol. Aug. 2008, 181:2330-2337.
Ouertatani-Sakouhi et al., "Kinetic-Based High-Throughput Screening Assay to Discover Novel Classes of Macrophage Migration Inhibitory Factor Inhibitors," J Biomol Screen, Epub Mar. 2010, 15:347-358.
Merck et al., "The D-dopachrome tautomerase (DDT) gene product is a cytokine and functional homologue of macrophage inhibitory factor (MIF)," Proc Natl Acad Sci USA, Epub Aug. 2011, 108:E577-585.
Schulte, "D-Dopachrome tautomerase (DDT) gene product is a cytokine and functional homologue of macrophage migration inhibitory factor (MIF)," PhD Thesis, Dec. 2011 (retrieved from the internet on May 15, 2012: //Darwin.bth.rwth-aachen.de/opus3/volltexte/2012/3882/pdf/3882.pdf).

*Primary Examiner* — Christine J Saoud
(74) *Attorney, Agent, or Firm* — Riverside Law LLP

(57) ABSTRACT

The present invention relates to the discovery that reduced levels of D-dopachrome tautomerase (D-DT) (also known as MIF-2) are associated with ischemia-reperfusion injury. Thus, the present invention relates to methods of administering D-DT and recombinant D-DT for the treatment of ischemia-reperfusion injury.

6 Claims, 15 Drawing Sheets

```
SEQUENCE LISTING

<160> NUMBER OF SEQ ID NOS: 2

<210> SEQ ID NO 1
<211> LENGTH: 19
<212> TYPE: DNA
<213> ORGANISM: Homo sapiens

<400> SEQUENCE: 1
tcaactatta cgacatgaa                                                  19

<210> SEQ ID NO 2
<211> LENGTH: 19
<212> TYPE: DNA
<213> ORGANISM: Homo sapiens

<400> SEQUENCE: 2
gcatgaccct gttgatgaa                                                  19
```

METHODS OF ADMINISTERING D-DOPACHROME TAUTOMERASE (D-DT) TO TREAT ISCHEMIA-REPERFUSION INJURY

CROSS-REFERENCE TO RELATED APPLICATION

This application is the U.S. national phase application filed under 35 U.S.C. §371 claiming benefit to International Patent Application No. PCT/US11/62062, filed on Nov. 23, 2011, which is entitled to priority under 35 U.S.C. §119(e) to U.S. Provisional Patent Application No. 61/416,904, filed on Nov. 24, 2010, all of which are hereby incorporated herein by reference in their entireties.

BACKGROUND OF THE INVENTION

Macrophage migration inhibitory factor (MIF) is the first cytokine activity described and a key regulatory mediator that is released upon activation of different cell types (Bloom, et al., 1966, Science 153:80-82; David, 1966, Proc Natl Acad Sci USA 56:72-77; Bernhagen, et al., 2003, Nature 365:756-759). MIF increases macrophage antimicrobial responses and it is expressed upstream of cytokines such as tumor necrosis factor (TNF)-α, IFN-γ, and IL-1β (Calandra, et al., 2003 Nat Rev Immunol 3:791-800). MIF activates immune cells by binding to CD74, leading to the recruitment of CD44 into a signaling complex, the stimulation of nonreceptor tyrosine kinases, and initiation of the ERK1/2 MAP kinase pathway (Shi, et al., 2006 Immunity 25:595-606; Leng, et al., 2003, J Exp Med 197:1467-1476). The chemokine receptors CXCR2 and CXCR4 also become activated by MIF via noncognate interactions that are reinforced in the presence of CD74 (Bernhagen, et al., 2007, Nat Med 13:587-596). Among mesenchymal cell types, MIF binding to cardiomyocyte CD74 stimulates the AMP-activated kinase (AMPK) cascade to mediate protection from ischemic injury (Miller, et al., 2008, Nature 451:578-582; Qi, et al., 2009, J Clin Invest 119: 3807-3816).

Although MIF receptor knockout mice (CD74−/−) phenocopy features MIF deficiency (Meyer-Siegler, et al., 2006, J Immunol 177:8730-8739; Topilski, et al., 2002, J Immunol 168:1610-1617), recent observations have led to the hypothesis that there may be a second ligand for CD74. MIF-deficient B cells, for example, are more sensitive to apoptosis than wild-type B cells, but the magnitude of this defect is twofold more pronounced in CD74-deficient cells (Gore, et al., 2008, J Biol Chem 283:2784-2792). Intravital microscopy studies also have shown a more pronounced effect of antagonism of CD74 than MIF in monocyte arrest (Bernhagen, et al., 2007, Nat Med 13:587-596). Anti-MIF antibodies, although highly effective in experimental studies, do not completely inhibit CD74-dependent cellular activation responses (Chagnon, et al., 2005, Circ Res 96:1095-1102).

D-dopachrome tautomerase (D-DT) (also known as MIF-2) and MIF show a conserved intron-exon structure and their coding regions are highly homologous. The genes for MIF and D-DT are in close apposition to each other and to two theta-class glutathione S-transferases, suggesting that these gene clusters arose by an ancestral duplication event. D-DT was named for its ability to tautomerize the nonnaturally occurring, D-stereoisomer of dopachrome, which is a catalytic property shared with MIF. This activity has been hypothesized to be a vestigial function that reflects MIF's ancestral origin in the invertebrate melanotic encapsulation response (Fingerle-Rowson, et al., 2009, Mol Cell Biol 29:1922-1932). A crystal structure of D-DT has verified its 3D similarity with MIF (Sugimoto, et al., 1999, Biochemistry 38:3268-3279). With the exception of recent studies indicating an interaction between the MIF and D-DT genes in the expression of proangiogenic factors and COX-2 in adenocarcinoma cell lines (Xin, et al., 2010, Mol Cancer Res 8:1601-1609; Coleman, et al., 2008, J Immunol 181:2330-2337), there have been no studies of the biologic functions of D-DT.

Despite the advances made in the art for detecting and treating inflammation associated with MIF signaling through CD74, there is a need in the art for the detection and treatment of inflammation associated with other molecules that signal through CD74. The present invention fulfills these needs.

SUMMARY OF THE INVENTION

The present invention relates to the discovery that altered levels of D-DT (also known as MIF-2) are associated with disorders and diseases. Thus, the present invention relates to compositions and methods useful for the assessment, diagnosis, characterization, prevention and treatment of disorders and diseases associated with an elevated level of D-DT. The present invention also relates to compositions and methods useful of the assessment, diagnosis, characterization, prevention and treatment of disorders and diseases associated with a reduced level of D-DT.

In one embodiment, the invention is a method of diagnosing a disease or disorder in a subject including the steps of: determining the level of D-DT in a biological sample from the subject, comparing the level of D-DT in the biological sample with a comparator control, and diagnosing the subject with a disease or disorder when the level of D-DT in the biological sample is different than the level of D-DT of the comparator control. In one embodiment, the level of D-DT in the biological sample is elevated when compared with the comparator control, while in another embodiment, the level of D-DT in the biological sample is reduced when compared with the comparator control. In one embodiment, the level of D-DT in the biological sample is determined by measuring the level of D-DT mRNA, while in another embodiment, the level of the level of D-DT in the biological sample is determined by measuring the level of D-DT polypeptide. In some embodiments, the level of D-DT in the biological sample is determined by measuring an enzymatic activity of D-DT polypeptide in the biological sample. In another embodiment, the level of D-DT in the biological sample is determined by measuring the binding of a detectable molecule to the D-DT enzyme substrate binding site. In a further embodiment, the level of D-DT in the biological sample is determined by measuring the displacement of a detectable molecule from the D-DT enzyme substrate binding site. In various embodiments, the comparator control is at least one selected from the group consisting of: a positive control, a negative control, a historical control, a historical norm, or the level of a reference molecule in the biological sample. In a particular embodiment, the reference molecule is MIF. The method of diagnosing a disease or disorder of the present invention useful in diagnosing a variety of diseases and disorders associated with D-DT, including, for example, infection, inflammatory disease, autoimmunity, cancer and ischemia-reperfusion injury. In preferred embodiments, the subject is human.

In another embodiment, the invention is a composition comprising a D-DT inhibitor. In various embodiments, the D-DT inhibitor is an antibody that specifically binds to D-DT, an antibody that specifically binds to D-DT and does not specifically bind to MIF, or an antibody that specifically binds to D-DT and also specifically binds to MIF. In various embodiments, the D-DT antibody is at least one of a polyclonal antibody, a monoclonal antibody, an intracellular antibody, an antibody fragment, a single chain antibody (scFv), a heavy chain antibody, a synthetic antibody, a chimeric antibody, and humanized antibody. In another embodiment, the D-DT inhibitor is an antisense nucleic acid. In some embodiments, the antisense nucleic acid is an siRNA or an miRNA. In a particular embodiment, the D-DT inhibitor is an siRNA comprising the nucleic acid sequence of SEQ ID NO: 2. In other various embodiments, the D-DT inhibitor is at least one of a chemical compound, a protein, a peptide, a peptidomemetic, a ribozyme, or a small molecule chemical compound.

In one embodiment, the invention is a method of treating a disease or disorder in a subject by administering to the subject a therapeutically effective amount of a composition comprising a D-DT inhibitor. In various embodiments, the D-DT inhibitor is an antibody that specifically binds to D-DT, an antibody that specifically binds to D-DT and does not specifically bind to MW, or an antibody that specifically binds to D-DT and also specifically binds to MIF. In various embodiments, the D-DT antibody is at least one of a polyclonal antibody, a monoclonal antibody, an intracellular antibody, an antibody fragment, a single chain antibody (scFv), a heavy chain antibody, a synthetic antibody, a chimeric antibody, and humanized antibody. In another embodiment, the D-DT inhibitor is an antisense nucleic acid. In some embodiments, the antisense nucleic acid is an siRNA or an miRNA. In a particular embodiment, the D-DT inhibitor is an siRNA comprising the nucleic acid sequence of SEQ ID NO: 2. In other various embodiments, the D-DT inhibitor is at least one of a chemical compound, a protein, a peptide, a peptidomemetic, a ribozyme, or a small molecule chemical compound. In various embodiments, the disease or disorder is at least one of infection, inflammatory disease, autoimmunity and cancer. In preferred embodiments, the subject is human.

In another embodiment, the invention is a method of preventing a disease or disorder in a subject by administering to the subject a therapeutically effective amount of composition comprising a D-DT inhibitor. In various embodiments, the D-DT inhibitor is an antibody that specifically binds to D-DT, an antibody that specifically binds to D-DT and does not specifically bind to MIF, or an antibody that specifically binds to D-DT and also specifically binds to MIF. In various embodiments, the D-DT antibody is at least one of a polyclonal antibody, a monoclonal antibody, an intracellular antibody, an antibody fragment, a single chain antibody (scFv), a heavy chain antibody, a synthetic antibody, a chimeric antibody, and humanized antibody. In another embodiment, the D-DT inhibitor is an antisense nucleic acid. In some embodiments, the antisense nucleic acid is an siRNA or an miRNA. In a particular embodiment, the D-DT inhibitor is an siRNA comprising the nucleic acid sequence of SEQ ID NO: 2. In other various embodiments, the D-DT inhibitor is at least one of a chemical compound, a protein, a peptide, a peptidomemetic, a ribozyme, or a small molecule chemical compound. In various embodiments, the disease or disorder is at least one of infection, inflammatory disease, autoimmunity and cancer. In preferred embodiments, the subject is human.

In one embodiment, the invention is a composition comprising a D-DT activator. In other various embodiments, the D-DT activator is at least one of a chemical compound, a protein, a peptide, a peptidomemetic, an antisense nucleic acid, a ribozyme, or a small molecule chemical compound.

In another embodiment, the invention is a method of treating ischemia-reperfusion injury in a subject by administering to the subject a therapeutically effective amount of a composition comprising at least one of a D-DT polypeptide, a recombinant D-DT polypeptide, an active D-DT polypeptide fragment, or a D-DT activator. In a preferred embodiment, the subject is a human.

In a further embodiment, the invention is a method of preventing ischemia-reperfusion injury in a subject by administering to the subject a therapeutically effective amount of a composition comprising at least one of a D-DT polypeptide, a recombinant D-DT polypeptide, an active D-DT polypeptide fragment, or a D-DT activator. In a preferred embodiment, the subject is a human.

In yet another embodiment, the invention is a method of preventing ischemia-reperfusion injury in a tissue or organ by administering to the tissue or organ a therapeutically effective amount of a composition comprising at least one selected from the group consisting of; a D-DT polypeptide, a recombinant D-DT polypeptide, an active D-DT polypeptide fragment, or a D-DT activator. In some embodiments, the tissue or organ is a pre-transplant tissue or organ. In a preferred embodiment, the tissue or organ is human.

In another embodiment, the invention is a method of identifying a test compound as a modulator of D-DT including the steps of: determining the level of D-DT in the presence of a test compound, determining the level of D-DT in the absence of a test compound, comparing the level of D-DT in the presence of the test compound with the level of D-DT in the absence of the test compound, and identifying the test compound as a modulator of D-DT when the level of D-DT in the presence of the test compound is different than the level of D-DT in the absence of the test compound. In some embodiments, the test compound is identified as a D-DT activator when the level of D-DT is higher in the presence of the test compound. In other embodiments, the test compound is identified as a D-DT inhibitor when the level of D-DT is lower in the presence of the test compound. In some embodiments, the level of D-DT is determined by measuring the level of D-DT mRNA. In other embodiments, the level of D-DT is determined by measuring the level of D-DT polypeptide. In some embodiments, the level of D-DT is determined by measuring an enzymatic activity of D-DT polypeptide. In certain embodiments, the enzymatic activity is tautomerase activity. In some embodiments, the level of D-DT is determined by measuring the binding of a detectable molecule to the D-DT enzyme substrate binding site. In other embodiments, the level of D-DT is determined by measuring the displacement of a detectable molecule from the D-DT enzyme substrate binding site. In various embodiments, the test compound is at least one on a chemical compound, a protein, a peptide, a peptidomemetic, an antibody, a nucleic acid, an antisense nucleic acid, a ribozyme, and a small molecule chemical compound.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1, comprising

FIG. 3, comprising

FIG. 4, comprising

FIG. 5, comprising

FIG. 6, comprising

FIG. 9B shows a comparison to incubation with MIF neutralizing antibody. p=0.05.

DETAILED DESCRIPTION OF THE INVENTION

Figure 1A:
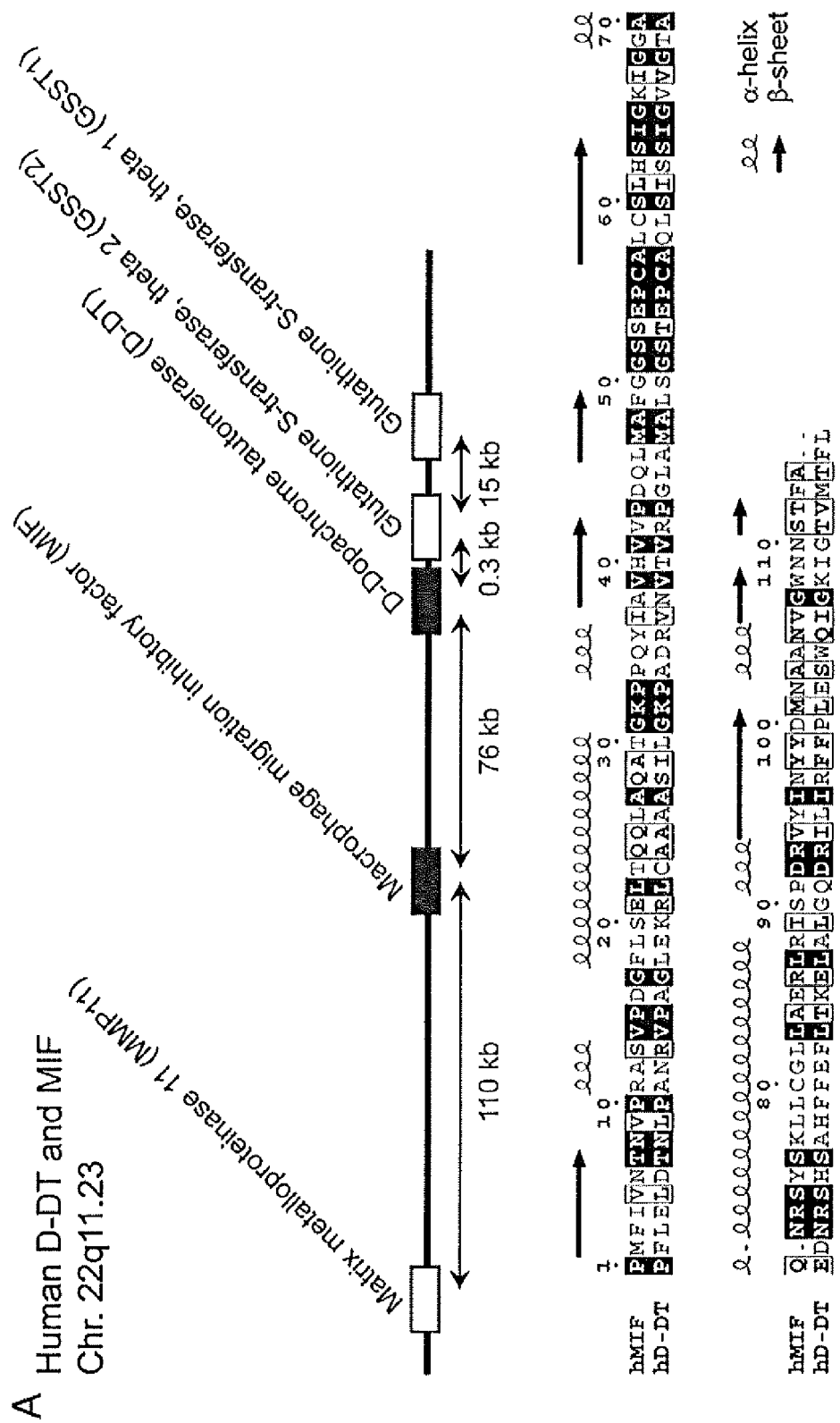
FIGS. 1A-1B, is a schematic depicting the genomic organization and protein homology of MIF and D-DT (also known as MIF-2). (A) Schematic diagrams showing the relationship between human MIF and D-DT with matrix metalloprotease 11 and GST genes (Upper) and the amino acid sequence and secondary structure homologies of the two proteins (Lower). (B) Mouse Mif, D-DT, and adjacent genes (Upper) and the corresponding amino acid sequence and secondary structure homologies of the two proteins (Lower). Gene structure was compiled from www.ensembl.org and sequence alignment performed using ClustalX and espript.ibcp.fr/ESPript/ESPript.

The present invention relates to the discovery that altered levels of D-DT (also known as MIF-2) are associated with disorders and diseases. Thus, the present invention relates to compositions and methods useful for the assessment, diagnosis, characterization, prevention and treatment of disorders and diseases associated with an elevated level of D-DT. The present invention also relates to compositions and methods useful of the assessment, diagnosis, characterization, prevention and treatment of disorders and diseases associated with a reduced level of D-DT.

In some embodiments, the compositions of the invention relate to inhibitors of D-DT. The methods of the invention include methods of diagnosing disorders and diseases associated with elevated levels of D-DT, as well as methods of monitoring the effectiveness of an applied treatment regimen of a disorder or disease associated with an elevated level of D-DT. In various embodiments, the disorders and diseases that can be diagnosed, assessed, characterized, prevented or treated using the compositions and methods of the invention include infection, inflammatory disease, autoimmunity and cancer.

In other embodiments, the compositions of the invention relate to activators of D-DT. The methods of the invention include methods of diagnosing disorders and diseases associated with reduced levels of D-DT, as well as methods of monitoring the effectiveness of an applied treatment regimen of a disorder or disease associated with a reduced level of D-DT. In various embodiments, the disorders and diseases that can be diagnosed, assessed, characterized, prevented or treated using the compositions and methods of the invention include ischemia-reperfusion injury.

DEFINITIONS

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

An "allele" refers to one specific form of a genetic sequence (such as a gene) within a cell, an individual or within a population, the specific form differing from other forms of the same gene in the sequence of at least one, and frequently more than one, variant sites within the sequence of the gene. The sequences at these variant sites that differ between different alleles are termed "variants." "polymorphisms," or "mutations."

As used herein, to "alleviate" a disease means reducing the frequency or severity of at least one sign or symptom of a disease or disorder.

As used herein the terms "alteration," "defect," "variation," or "mutation," refers to a mutation in a gene in a cell that affects the function, activity, expression (transcription or translation) or conformation of the polypeptide that it encodes. Mutations encompassed by the present invention can be any mutation of a gene in a cell that results in the enhancement or disruption of the function, activity, expression or conformation of the encoded polypeptide, including the complete absence of expression of the encoded protein and can include, for example, missense and nonsense mutations, insertions, deletions, frameshifts and premature terminations. Without being so limited, mutations encompassed by the present invention may alter splicing the mRNA (splice site mutation) or cause a shift in the reading frame (frameshift).

The term "amplification" refers to the operation by which the number of copies of a target nucleotide sequence present in a sample is multiplied.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. The antibodies in the present invention may exist in a variety of forms including, for example, polyclonal antibodies, monoclonal antibodies, intracellular antibodies ("intrabodies"), Fv, Fab and F(ab)$_2$, as well as single chain antibodies (scFv), heavy chain antibodies, such as camelid antibodies, synthetic antibodies, chimeric antibodies, and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc, Natl. Acad. Sci. USA 85:5879-5883; Bird et al., 1988, Science 242:423-426).

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. K and light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

As used herein, an "immunoassay" refers to any binding assay that uses an antibody capable of binding specifically to a target molecule to detect and quantify the target molecule.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

By the term "applicator," as the term is used herein, is meant any device including, but not limited to, a hypodermic syringe, a pipette, an iontophoresis device, a patch, and the like, for administering the compositions of the invention to a subject.

The term "auto-antigen" means, in accordance with the present invention, any self-antigen which is mistakenly recognized by the immune system as being foreign. Auto-antigens comprise, but are not limited to, cellular proteins, phosphoproteins, cellular surface proteins, cellular lipids, nucleic acids, glycoproteins, including cell surface receptors.

The term "cancer," or "neoplasm" as used herein includes, but is not limited to, benign and malignant cancers of the oral cavity (e.g., mouth, tongue, pharynx, etc.), digestive system (e.g., esophagus, stomach, small intestine, colon, rectum, liver, bile duct, gall bladder, pancreas, etc.), respiratory system (e.g., larynx, lung, bronchus, etc.), bones, joints, skin (e.g., basal cell, squamous cell, melanoma, etc.), breast, genital system, (e.g., uterus, ovary, prostate, testis, etc.), urinary system (e.g, bladder, kidney, ureter, etc.), eye, nervous system (e.g., brain, etc.), endocrine system (e.g., thyroid, etc.), and hematopoietic system (e.g., lymphoma, myeloma, leukemia, acute lymphocytic leukemia, chronic lymphocytic leukemia, acute myeloid leukemia, chronic myeloid leukemia, etc.).

The term "coding sequence," as used herein, means a sequence of a nucleic acid or its complement, or a part thereof, that can be transcribed and/or translated to produce the mRNA and/or the polypeptide or a fragment thereof. Coding sequences include exons in a genomic DNA or immature primary RNA transcripts, which are joined together by the cell's biochemical machinery to provide a mature mRNA. The anti-sense strand is the complement of such a nucleic acid, and the coding sequence can be deduced therefrom. In contrast, the term "non-coding sequence," as used herein, means a sequence of a nucleic acid or its complement, or a part thereof, that is not translated into amino acid in vivo, or where tRNA does not interact to place or attempt to place an amino acid. Non-coding sequences include both intron sequences in genomic DNA or immature primary RNA transcripts, and gene-associated sequences such as promoters, enhancers, silencers, and the like.

As used herein, the terms "complementary" or "complementarity" are used in reference to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

As used herein, the term "diagnosis" refers to the determination of the presence of a disease or disorder. In some embodiments of the present invention, methods for making a diagnosis are provided which permit determination of a the presence of a particular disease or disorder.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" as used herein, means an amount which provides a therapeutic or prophylactic benefit.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein, the term "fragment," as applied to a nucleic acid, refers to a subsequence of a larger nucleic acid. A "fragment" of a nucleic acid can be at least about 15 nucleotides in length; for example, at least about 50 nucleotides to about 100 nucleotides; at least about 100 to about 500 nucleotides, at least about 500 to about 1000 nucleotides; at least about 1000 nucleotides to about 1500 nucleotides; about 1500 nucleotides to about 2500 nucleotides; or about 2500 nucleotides (and any integer value in between). As used herein, the term "fragment," as applied to a protein or peptide, refers to a subsequence of a larger protein or peptide. A "fragment" of a protein or peptide can be at least about 20 amino acids in length; for example, at least about 50 amino acids in length; at least about 100 amino acids in length; at least about 200 amino acids in length; at least about 300 amino acids in length; or at least about 400 amino acids in length (and any integer value in between).

The term "gene" refers to a nucleic acid (e.g., DNA) sequence that includes coding sequences necessary for the production of a polypeptide, precursor, or RNA (e.g., mRNA). The polypeptide may be encoded by a full length coding sequence or by any portion of the coding sequence so long as the desired activity or functional property (e.g., enzymatic activity, ligand binding, signal transduction, immunogenicity, etc.) of the full-length or fragment is retained. The term also encompasses the coding region of a structural gene and the sequences located adjacent to the coding region on both the 5' and 3' ends for a distance of about 2 kb or more on either end such that the gene corresponds to the length of the full-length mRNA and 5' regulatory sequences which influence the transcriptional properties of the gene. Sequences located 5' of the coding region and present on the mRNA are referred to as 5'-untranslated sequences. The 5'-untranslated sequences usually contain the regulatory sequences. Sequences located 3' or downstream of the coding region and present on the mRNA are referred to as 3'-untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

A "genome" is all the genetic material of an organism. In some instances, the term genome may refer to the chromosomal DNA. Genome may be multichromosomal such that the DNA is cellularly distributed among a plurality of individual chromosomes. For example, in human there are 22 pairs of chromosomes plus a gender associated XX or XY pair, DNA derived from the genetic material in the chromosomes of a particular organism is genomic DNA. The term genome may also refer to genetic materials from organisms that do not have chromosomal structure. In addition, the term genome may refer to mitochondria DNA. A genomic library is a collection of DNA fragments representing the whole or a portion of a genome. Frequently, a genomic library is a collection of clones made from a set of randomly generated, sometimes overlapping DNA fragments representing the entire genome or a portion of the genome of an organism.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared ×100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

The term "housekeeping gene" as used herein refers to genes that are generally always expressed and thought to be involved in routine cellular metabolism. Housekeeping genes are well known and include such genes as glyceraldehyde-3-phosphate dehydrogenase (G3PDH or GAPDH), albumin, actins, tubulins, cyclophilin, hypoxanthine phsophoribosyl-transferase (HRPT), 28S, and 18S rRNAs and the like.

As used herein, the term "hybridization" is used in reference to the pairing of complementary nucleic acids. Hybridization and the strength of hybridization (i.e., the strength of the association between the nucleic acids) is impacted by such factors as the degree of complementarity between the nucleic acids, stringency of the conditions involved, the $T_m$ of the formed hybrid, and the G:C ratio within the nucleic acids. A single molecule that contains pairing of complementary nucleic acids within its structure is said to be "self-hybridized." A single DNA molecule with internal complementarity could assume a variety of secondary structures including loops, kinks or, for long stretches of base pairs, coils.

The term "immunoglobulin" or "Ig," as used herein is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

"Instructional material," as that term is used herein, includes a publication, a recording, a diagram, or any other medium of expression which can be used to communicate the usefulness of the nucleic acid, peptide, and/or compound of the invention in the kit for identifying, diagnosing or alleviating or treating the various diseases or disorders recited herein. Optionally, or alternately, the instructional material may describe one or more methods of identifying, diagnosing or alleviating the diseases or disorders in a cell or a tissue of a subject. The instructional material of the kit may, for example, be affixed to a container that contains the nucleic acid, peptide, and/or compound of the invention or be shipped together with a container that contains the nucleic acid, peptide, and/or compound. Alternatively, the instructional material may be shipped separately from the container with the intention that the recipient uses the instructional material and the compound cooperatively.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

The term "label" when used herein refers to a detectable compound or composition that is conjugated directly or indirectly to a probe to generate a "labeled" probe. The label may be detectable by itself (e.g. radioisotope labels or fluorescent labels) or, in the case of an enzymatic label, may catalyze chemical alteration of a substrate compound or composition that is detectable (e.g., avidin-biotin). In some instances, primers can be labeled to detect a PCR product.

The terms "microarray" and "array" refers broadly to "DNA microarrays," "DNA chip(s)," "protein microarrays" and "protein chip(s)" and encompasses all art-recognized solid supports, and all art-recognized methods for affixing nucleic acid, peptide, and polypeptide molecules thereto. Preferred arrays typically comprise a plurality of different nucleic acid or peptide probes that are coupled to a surface of a substrate in different, known locations. These arrays, also described as "microarrays" or colloquially "chips" have been generally described in the art, for example, U.S. Pat. Nos. 5,143,854, 5,445,934, 5,744,305, 5,677,195, 5,800,992, 6,040,193, 5,424,186 and Fodor et al., 1991, Science, 251: 767-777, each of which is incorporated by reference in its entirety for all purposes. Arrays may generally be produced using a variety of techniques, such as mechanical synthesis methods or light directed synthesis methods that incorporate a combination of photolithographic methods and solid phase synthesis methods. Techniques for the synthesis of these arrays using mechanical synthesis methods are described in, e.g., U.S. Pat. Nos. 5,384,261, and 6,040,193, which are incorporated herein by reference in their entirety for all purposes. Although a planar array surface is preferred, the array may be fabricated on a surface of virtually any shape or even a multiplicity of surfaces. Arrays may be nucleic acids on beads, gels, polymeric surfaces, fibers such as fiber optics, glass or any other appropriate substrate. (See U.S. Pat. Nos. 5,770,358, 5,789,162, 5,708,153, 6,040,193 and 5,800,992, which are hereby incorporated by reference in their entirety for all purposes.) Arrays may be packaged in such a manner as to allow for diagnostic use or can be an all-inclusive device; e.g., U.S. Pat. Nos. 5,856,174 and 5,922,591 incorporated in their entirety by reference for all purposes. Arrays are commercially available from, for example, Affymetrix (Santa Clara, Calif.) and Applied Biosystems (Foster City, Calif.), and are directed to a variety of purposes, including genotyping, diagnostics, mutation analysis, marker expression, and gene expression monitoring for a variety of eukaryotic and prokaiyotic organisms. The number of probes on a solid support may be varied by changing the size of the individual features. In one embodiment the feature size is 20 by 25 microns square, in other embodiments features may be, for example, 8 by 8, 5 by 5 or 3 by 3 microns square, resulting in about 2,600,000, 6,600,000 or 18,000,000 individual probe features.

Assays for amplification of the known sequence are also disclosed. For example primers for PCR may be designed to amplify regions of the sequence. For RNA, a first reverse transcriptase step may be used to generate double stranded DNA from the single stranded RNA. The array may be designed to detect sequences from an entire genome; or one or more regions of a genome, for example, selected regions of a genome such as those coding for a protein or RNA of interest; or a conserved region from multiple genomes; or multiple genomes, arrays and methods of genetic analysis using arrays is described in Cutler, et al., 2001, Genome Res. 11(11): 1913-1925 and Warrington, et al., 2002, Hum Mutat 19:402-409 and in US Patent Pub No 20030124539, each of which is incorporated herein by reference in its entirety.

By the term "modulating," as used herein, is meant mediating a detectable increase or decrease in the level of a mRNA, polypeptide, or a response in a subject compared with the level of a mRNA, polypeptide or a response in the subject in the absence of a treatment or compound, and/or compared with the level of a mRNA, polypeptide, or a response in an otherwise identical but untreated subject. The term encompasses perturbing and/or affecting a native signal or response thereby mediating a beneficial therapeutic response in a subject, preferably, a human.

A "mutation," as used herein, refers to a change in nucleic acid or polypeptide sequence relative to a reference sequence (which is preferably a naturally-occurring normal or "wild-type" sequence), and includes translocations, deletions, insertions, and substitutions/point mutations. A "mutant" as used herein, refers to either a nucleic acid or protein comprising a mutation.

A "nucleic acid" refers to a polynucleotide and includes poly-ribonucleotides and poly-deoxyribonucleotides. Nucleic acids according to the present invention may include any polymer or oligomer of pyrimidine and purine bases, preferably cytosine, thymine, and uracil, and adenine and guanine, respectively. (See Albert L, Lehninger, Principles of Biochemistry, at 793-800 (Worth Pub. 1982) which is herein incorporated in its entirety for all purposes). Indeed, the present invention contemplates any deoxyribonucleotide, ribonucleotide or peptide nucleic acid component, and any chemical variants thereof; such as methylated, hydroxymethylated or glucosylated forms of these bases, and the like. The polymers or oligomers may be heterogeneous or homogeneous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

An "oligonucleotide" or "polynucleotide" is a nucleic acid ranging from at least 2, preferably at least 8, 15 or 25 nucleotides in length, but may be up to 50, 100, 1000, or 5000 nucleotides long or a compound that specifically hybridizes to a polynucleotide. Polynucleotides include sequences of deoxyribonucleic acid (DNA) or ribonucleic acid (RNA) or mimetics thereof which may be isolated from natural sources, recombinantly produced or artificially synthesized. A further example of a polynucleotide of the present invention may be a peptide nucleic acid (PNA). (See U.S. Pat. No. 6,156,501 which is hereby incorporated by reference in its entirety.) The invention also encompasses situations in which there is a nontraditional base pairing such as Hoogsteen base pairing which has been identified in certain tRNA molecules and postulated to exist in a triple helix, "Polynucleotide" and "oligonucleotide" are used interchangeably in this disclosure. It will be understood that when a nucleotide sequence is represented herein by a DNA sequence (e.g., A, T, G, and C), this also includes the corresponding RNA sequence (e.g., A, U, G, C) in which "U" replaces "T".

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

As used herein, the term "polymerase chain reaction" ("PCR") refers to the method of K. B. Mullis (U.S. Pat. Nos. 4,683,195 4,683,202, and 4,965,188, hereby incorporated by reference), which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified". As used herein, the terms "PCR product," "PCR fragment," "amplification product" or "amplicon" refer to the resultant mixture of compounds after two or more cycles of the PCR steps of denaturation, annealing and extension are complete. These terms encompass the case where there has been amplification of one or more segments of one or more target sequences.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences.

The term "perfect match," "match," "perfect match probe" or "perfect match control" refers to a nucleic acid that has a sequence that is perfectly complementary to a particular target sequence. The nucleic acid is typically perfectly complementary to a portion (subsequence) of the target sequence. A perfect match (PM) probe can be a "test probe," a "normalization control" probe, an expression level control probe and the like. A perfect match control or perfect match is, however, distinguished from a "mismatch" or "mismatch probe." The term "mismatch," "mismatch control" or "mismatch probe" refers to a nucleic acid whose sequence is not perfectly complementary to a particular target sequence. As a non-limiting example, for each mismatch (MM) control in a high-density probe array there typically exists a corresponding perfect match (PM) probe that is perfectly complementary to the same particular target sequence. The mismatch may comprise one or more bases. While the mismatch(es) may be located anywhere in the mismatch probe, terminal mismatches are less desirable because a terminal mismatch is less likely to prevent hybridization of the target sequence. In a particularly preferred embodiment, the mismatch is located at or near the center of the probe such that the mismatch is most likely to destabilize the duplex with the target sequence under the test hybridization conditions.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

As used herein, "polynucleotide" includes cDNA, RNA, DNA/RNA hybrid, antisense RNA, ribozyme, genomic DNA, synthetic forms, and mixed polymers, both sense and antisense strands, and may be chemically or biochemically modified to contain non-natural or derivatized, synthetic, or semi-synthetic nucleotide bases. Also, contemplated are alterations of a wild type or synthetic gene, including but not limited to deletion, insertion, substitution of one or more nucleotides, or fusion to other polynucleotide sequences.

The term "primer" refers to an oligonucleotide capable of acting as a point of initiation of synthesis along a complementary strand when conditions are suitable for synthesis of a primer extension product. The synthesizing conditions include the presence of four different deoxyribonucleotide triphosphates and at least one polymerization-inducing agent such as reverse transcriptase or DNA polymerase. These are present in a suitable buffer, which may include constituents which are co-factors or which affect conditions such as pH and the like at various suitable temperatures. A primer is preferably a single strand sequence, such that amplification efficiency is optimized, but double stranded sequences can be utilized.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The term "reaction mixture" or "PCR reaction mixture" or "master mix" or "master mixture" refers to an aqueous solution of constituents in a PCR reaction that can be constant across different reactions. An exemplary PCR reaction mixture includes buffer, a mixture of deoxyribonucleoside triphosphates, primers, probes, and DNA polymerase. Generally, template RNA or DNA is the variable in a PCR.

"Sample" or "biological sample" as used herein means a biological material isolated from a subject. The biological sample may contain any biological material suitable for detecting a mRNA, polypeptide or other marker of a physiologic or pathologic process in a subject, and may comprise fluid, tissue, cellular and/or non-cellular material obtained from the individual.

As used herein the term "stringency" is used in reference to the conditions of temperature, ionic strength, and the presence of other compounds such as organic solvents, under which nucleic acid hybridizations are conducted. Under "low stringency conditions" a nucleic acid sequence of interest will hybridize to its exact complement, sequences with single base mismatches, closely related sequences (e.g., sequences with 90% or greater homology), and sequences having only partial homology (e.g., sequences with 50-90% homology). Under "medium stringency conditions," a nucleic acid sequence of interest will hybridize only to its exact complement, sequences with single base mismatches, and closely related sequences (e.g., 90% or greater homology). Under "high stringency conditions," a nucleic acid sequence of interest will hybridize only to its exact complement, and (depending on conditions such a temperature) sequences with single base mismatches. In other words, under conditions of high stringency the temperature can be raised so as to exclude hybridization to sequences with single base mismatches.

As used herein, "substantially purified" refers to being essentially free of other components. For example, a substantially purified cell is a cell which has been separated from other cell types with which it is normally associated in its naturally occurring state. In some instances, a population of substantially purified cells refers to a homogenous population of cells. In other instances, this term refers simply to a cell that have been separated from the cells with which they are naturally associated in their natural state.

The term "target" as used herein refers to a molecule that has an affinity for a given probe. Targets may be naturally-occurring or man-made molecules. Also, they can be employed in their unaltered state or as aggregates with other species. Targets may be attached, covalently or noncovalently, to a binding member, either directly or via a specific binding substance. Targets are sometimes referred to in the art as anti-probes. As the term targets is used herein, no difference in meaning is intended.

As used herein, the terms "therapy" or "therapeutic regimen" refer to those activities taken to alleviate or alter a disorder or disease state, e.g., a course of treatment intended to reduce or eliminate at least one sign or symptom of a disease or disorder using pharmacological, surgical, dietary and/or other techniques. A therapeutic regimen may include a prescribed dosage of one or more drugs or surgery. Therapies will most often be beneficial and reduce or eliminate at least one sign or symptom of the disorder or disease state, but in some instances the effect of a therapy will have non-desirable or side-effects. The effect of therapy will also be impacted by the physiological state of the subject, e.g., age, gender, genetics, weight, other disease conditions, etc.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

To "treat" a disease as the term is used herein, means to reduce the frequency or severity of at least one sign or symptom of a disease or disorder experienced by a subject.

As used herein, the term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and/or functional properties (i.e., altered characteristics) when compared to the wild-type gene or gene product. It is noted that naturally occurring mutants can be isolated; these are identified by the fact that they have altered characteristics (including altered nucleic acid sequences) when compared to the wild-type gene or gene product.

DESCRIPTION

The present invention relates to the discovery that altered levels of D-DT (also known as MIF-2) are associated with disorders and diseases. Thus, the present invention relates to compositions and methods useful for the assessment, diagnosis, characterization, prevention and treatment of disorders and diseases associated with an elevated level of D-DT. The present invention also relates to compositions and methods useful of the assessment, diagnosis, characterization, prevention and treatment of disorders and diseases associated with a reduced level of D-DT.

In some embodiments, the compositions of the invention relate to inhibitors of D-DT. The methods of the invention include methods of diagnosing disorders and diseases associated with elevated levels of D-DT, as well as methods of monitoring the effectiveness of an applied treatment regimen of a disorder or disease associated with an elevated level of D-DT. In various embodiments, the disorders and diseases that can be diagnosed, assessed, characterized, prevented or treated using the compositions and methods of the invention include infection, inflammatory disease, autoimmunity and cancer. By way of non-limiting examples, the disorders and diseases that can be diagnosed, assessed, characterized, prevented or treated using the compositions and methods of the invention include: asthma, atheroma, atherosclerosis, autism, autoinflammatory disease, autoimmune myocarditis, autoimmune hepatitis, bacterial infection, cancer, celiac disease, cellular proliferative disorder, Crohn's disease, colitis, diabetes, dermatitis, diverticulitis, dry age-related macular degeneration (AMD), endotoxemia, glomerulonephritis, graft versus host disease, Guillain-Barre syndrome, heart disease, hepatitis, inflammation, inflammatory breast cancer, inflammatory demyelinating polyneuropathy, intestinal cystitis, irritable bowel disease (IBD), lupus erythematous, microbial infection, multiple sclerosis, neoplasia, ovarian cancer, pelvic inflammatory disease (ND), prostatitis, psoriasis, reperfusion injury, rheumatoid arthritis, sarcoidosis, sepsis, septic shock, transplant rejection, trauma-induced inflammation, ulcerative colitis, vasculitis, Wegener's granulomatous and wet age-related macular degeneration (AMD).

The present invention also relates to the discovery that signaling by D-DT through CD74 activates AMPK in cardiomyocytes. Thus, in other embodiments, the compositions of the invention relate to activators of D-DT. The methods of the invention include methods of diagnosing disorders and diseases associated with reduced levels of D-DT, as well as methods of monitoring the effectiveness of an applied treatment regimen of a disorder or disease associated with a reduced level of D-DT. In various embodiments, the disorders and diseases that can be diagnosed, assessed, characterized, prevented or treated using the compositions and methods of the invention include ischemia-reperfusion injury in, for example, the heart and other solid organs, including, but not limited to, the kidney, the liver and the brain.

Assays

The present invention relates to the discovery that altered levels of D-DT are associated with infection, inflammatory disease, autoimmunity, cancer and ischemia-reperfusion injury. In some embodiments, the invention relates to a screening assay of a subject to determine whether the subject has an elevated level of D-DT. In other embodiments, the invention relates to a screening assay of a subject to determine whether the subject has a reduced level of D-DT. The present invention provides methods of assessing the level of D-DT in a subject. In various embodiments, the level of D-DT in the biological sample can be determined by assessing the amount of D-DT polypeptide present in the biological sample, the amount of D-DT mRNA present in the biological sample, the amount of D-DT enzymatic activity in the biological sample, the amount of D-DT receptor binding activity in the biological sample, or a combination thereof.

The present invention also provides methods of diagnosing a subject having an elevated level of D-DT, with a disease or disorder, such as infection, inflammatory disease, autoimmunity and cancer. Further, the present invention provides methods of diagnosing a subject having a reduced level of D-DT, with a disease or disorder, such as ischemia-reperfusion injury.

In one embodiment, the method of the invention is a diagnostic assay for diagnosing infection, inflammatory disease, autoimmunity or cancer in a subject in need thereof, by determining whether the level of D-DT is increased in a biological sample obtained from the subject. In various embodiments, to determine whether the level of D-DT is increased in a biological sample obtained from the subject, the level of D-DT is compared with the level of at least one comparator control, such as a positive control, a negative control, a historical control, a historical norm, or the level of another reference molecule in the biological sample. In one embodiment, the reference molecule in the biological sample is MIF. In certain embodiments, the ratio of D-DT and MIF is determined to aid in the diagnosis. The results of the diagnostic assay can be used alone, or in combination with other information from the subject, or other information from the biological sample obtained from the subject.

In another embodiment, the method of the invention is a diagnostic assay for diagnosing ischemia-reperfusion injury in a subject in need thereof, by determining whether the level of D-DT is reduced in a biological sample obtained from the subject. In various embodiments, to determine whether the level of D-DT is reduced in a biological sample obtained from the subject, the level of D-DT is compared with the level of at least one comparator control, such as a positive control, a negative control, a historical control, a historical norm, or the level of another reference molecule in the biological sample. In one embodiment, the reference molecule in the biological sample is MIF. In certain embodiments, the ratio of D-DT and MIF is determined to aid in the diagnosis. The results of the diagnostic assay can be used alone, or in combination with other information from the subject, or other information from the biological sample obtained from the subject.

In a further embodiment, the method of the invention is an assay for monitoring the effectiveness of a treatment administered to a subject in need thereof, by determining whether the level of D-DT in a biological sample obtained from the subject is modulated upon administration of the treatment. The assay can be performed before, during or after a treatment has been administered, or any combination thereof. In various embodiments, to determine whether the level of D-DT is modulated in a biological sample obtained from the subject, the level of D-DT is compared with the level of at least one comparator control, such as a positive control, a negative control, a historical control, a historical norm, or the level of another reference molecule in the biological sample. In one embodiment, the reference molecule in the biological sample is MIF. In certain embodiments, the ratio of D-DT and MIF is determined to aid in the monitoring of the treatment. The results of the assay can be used alone, or in combination with other information from the subject, or other information from the biological sample obtained from the subject.

In various embodiments of the assays of the invention, the level of D-DT is determined to be elevated when the level of D-DT is increased by at least 10%, by at least 20%, by at least 30%, by at least 40%, by at least 50%, by at least 60%, by at least 70%, by at least 80%, by at least 90%, by at least 100%, by at least 125%, by at least 150%, by at least 175%, by at least 200%, by at least 250%, by at least 300%, by at least 400%, by at least 500%, by at least 600%, by at least 700%, by at least 800%, by at least 900%, by at least 1000%, by at least 1500%, by at least 2000%, by at least 2500%, by at least 3000%, by at least 4000%, or by at least 5000%, when compared with a comparator control.

In other various embodiments of the assays of the invention, the level of D-DT is determined to be reduced when the level of D-DT is reduced by at least 10%, by at least 20%, by at least 30%, by at least 40%, by at least 50%, by at least 60%, by at least 70%, by at least 80%, by at least 90%, by at least 100%, by at least 125%, by at least 150%, by at least 175%, by at least 200%, by at least 250%, by at least 300%, by at least 400%, by at least 500%, by at least 600%, by at least 700%, by at least 800%, by at least 900%, by at least 1000%, by at least 1500%, by at least 2000%, by at least 2500%, by at least 3000%, by at least 4000%, or by at least 5000%, when compared with a comparator control.

In the assay methods of the invention, a test biological sample from a subject is assessed for the level of D-DT in the biological sample obtained from the patient. The level of D-DT in the biological sample can be determined by assessing the amount of D-DT polypeptide in the biological sample, the amount of D-DT mRNA in the biological sample, the amount of D-DT enzymatic activity in the biological sample, the amount of D-DT receptor binding activity in the biological sample, or a combination thereof. In one embodiment, the D-DT enzymatic activity assessed is D-DT tautomerization activity. In another embodiment, the D-DT enzymatic activity assessed is D-DT tautomerization of p-hydroxyphenylpyruvate (HPP). In various embodiments, the subject is a human subject, and may be of any race, sex and age. Representative subjects include those who are suspected of having infection, inflammatory disease, autoimmunity or cancer, those who have been diagnosed with infection, inflammatory disease, autoimmunity or cancer, those who have infection, inflammatory disease, autoimmunity or cancer, those who have had infection, inflammatory disease, autoimmunity or cancer, those who at risk of a recurrence of infection, inflammatory disease, autoimmunity or cancer, and those who are at risk of developing infection, inflammatory disease, autoimmunity or cancer.

In various embodiments, the test sample is a sample containing at least a fragment of a D-DT polypeptide or a D-DT nucleic acid. The term, "fragment," as used herein, indicates that the portion of the polypeptide, mRNA or cDNA is of a length that is sufficient to identify the fragment as D-DT.

The test sample is prepared from a biological sample obtained from the subject. The biological sample can be a sample from any source which contains a polypeptide or a nucleic acid, such as a body fluid or a tissue, or a combination thereof. A biological sample can be obtained by appropriate methods, such as, by way of examples, blood draw, fluid draw, or biopsy. A biological sample can be used as the test sample; alternatively, a biological sample can be processed to enhance access to the polypeptides or nucleic acids, or copies of the nucleic acids, and the processed biological sample can then be used as the test sample. For example, in various embodiments, nucleic acid (e.g., mRNA, cDNA prepared from mRNA, etc.) is prepared from a biological sample, for use in the methods. Alternatively or in addition, if desired, an amplification method can be used to amplify nucleic acids comprising all or a fragment of a mRNA in a biological sample, for use as the test sample in the assessment of the level of D-DT in the biological sample.

In various embodiments of the invention, methods of measuring D-DT polypeptide levels in a biological sample obtained from a patient include, but are not limited to, an immunochromatography assay, an immunodot assay, a Luminex assay, an ELISA assay, an ELISPOT assay, a protein microarray assay, a ligand-receptor binding assay, displacement of a ligand from a receptor assay, displacement of a ligand from a shared receptor assay, an immunostaining assay, a Western blot assay, a mass spectrophotometry assay, a radioimmunoassay (RIA), a radioimmunodiffusion assay, a liquid chromatography-tandem mass spectrometry assay, an ouchterlony immunodiffusion assay, reverse phase protein microarray, a rocket immunoelectrophoresis assay, an immunohistostaining assay, an immunoprecipitation assay, a complement fixation assay, FACS, an enzyme-substrate binding assay, an enzymatic assay, an enzymatic assay employing a detectable molecule, such as a chromophore, fluorophore, or radioactive substrate, a substrate binding assay employing such a substrate, a substrate displacement assay employing such a substrate, and a protein chip assay (see also, 2007, Van Emon, Immunoassay and Other Bioanalytical Techniques, CRC Press; 2005, Wild, Immunoassay Handbook, Gulf Professional Publishing; 1996, Diamandis and Christopoulos, Immunoassay, Academic Press; 2005, Joos, Microarrays in Clinical Diagnosis, Humana Press; 2005, Hamdan and Righetti, Proteomics Today, John Wiley and Sons; 2007).

In some embodiments, quantitative hybridization methods, such as Southern analysis, Northern analysis, or in situ hybridizations, can be used (see Current Protocols in Molecular Biology, Ausubel, F. et al., eds., John Wiley & Sons, including all supplements). A "nucleic acid probe," as used herein, can be a DNA probe or an RNA probe. The probe can be, for example, a gene, a gene fragment (e.g., one or more exons), a vector comprising the gene, a probe or primer, etc. For representative examples of use of nucleic acid probes, see, for example, U.S. Pat. Nos. 5,288,611 and 4,851,330. The nucleic acid probe can be, for example, a full-length nucleic acid molecule, or a portion thereof, such as an oligonucleotide of at least 15, 30, 50, 100, 250 or 500 nucleotides in length and sufficient to specifically hybridize under stringent conditions to appropriate target mRNA or cDNA. The hybridization sample is maintained under conditions which are sufficient to allow specific hybridization of the nucleic acid probe to mRNA or cDNA. Specific hybridization can be performed under high stringency conditions or moderate stringency conditions, as appropriate. In a preferred embodiment, the hybridization conditions for specific hybridization are high stringency. Specific hybridization, if present, is then detected using standard methods. If specific hybridization occurs between the nucleic acid probe having a mRNA or cDNA in the test sample, the level of the mRNA or cDNA in the sample can be assessed. More than one nucleic acid probe can also be used concurrently in this method. Specific hybridization of any one of the nucleic acid probes is indicative of the presence of the mRNA or cDNA of interest, as described herein.

Alternatively, a peptide nucleic acid (PNA) probe can be used instead of a nucleic acid probe in the quantitative hybridization methods described herein. PNA is a DNA mimic having a peptide-like, inorganic backbone, such as N-(2-aminoethyl)glycine units, with an organic base (A, G, C, T or U) attached to the glycine nitrogen via a methylene carbonyl linker (see, for example, 1994, Nielsen et al., Bioconjugate Chemistry 5:1). The PNA probe can be designed to specifically hybridize to a target nucleic acid sequence. Hybridization of the PNA probe to a nucleic acid sequence is used to determine the level of the target nucleic acid in the biological sample.

In another embodiment, arrays of oligonucleotide probes that are complementary to target nucleic acid sequences in the biological sample obtained from a subject can be used to determine the level of D-DT in the biological sample obtained from a subject. The array of oligonucleotide probes can be used to determine the level of D-DT alone, or the level of D-DT in relation to the level of one or more other nucleic acids in the biological sample. Oligonucleotide arrays typically comprise a plurality of different oligonucleotide probes that are coupled to a surface of a substrate in different known locations. These oligonucleotide arrays, also known as "Genechips," have been generally described in the art, for example, U.S. Pat. No. 5,143,854 and PCT patent publication Nos. WO 90/15070 and 92/10092. These arrays can generally be produced using mechanical synthesis methods or light directed synthesis methods which incorporate a combination of photolithographic methods and solid phase oligonucleotide synthesis methods. See Fodor et al., Science, 251:767-777 (1991), Pirrung et al., U.S. Pat. No. 5,143,854 (see also PCT Application No. WO 90/15070) and Fodor et al., PCT Publication No. WO 92/10092 and U.S. Pat. No. 5,424,186. Techniques for the synthesis of these arrays using mechanical synthesis methods are described in, e.g., U.S. Pat. No. 5,384,261.

After an oligonucleotide array is prepared, a nucleic acid of interest is hybridized with the array and its level is quantified. Hybridization and quantification are generally carried out by methods described herein and also in, e.g., published PCT Application Nos. WO 92/10092 and WO 95/11995, and U.S. Pat. No. 5,424,186. In brief, a target nucleic acid sequence is amplified by well-known amplification techniques, e.g., PCR. Typically, this involves the use of primer sequences that are complementary to the target nucleic acid. Asymmetric PCR techniques may also be used. Amplified target, generally incorporating a label, is then hybridized with the array under appropriate conditions. Upon completion of hybridization and washing of the array, the array is scanned to determine the quantity of hybridized nucleic acid. The hybridization data obtained from the scan is typically in the form of fluorescence intensities as a function of quantity, or relative quantity, of the target nucleic acid in the biological sample. The target nucleic acid can be hybridized to the array in combination with one or more comparator controls (e.g., positive control, negative control, quantity control, etc.) to improve quantification of the target nucleic acid in the sample.

The probes and primers according to the invention can be labeled directly or indirectly with a radioactive or nonradioactive compound, by methods well known to those skilled in the art, in order to obtain a detectable and/or quantifiable signal; the labeling of the primers or of the probes according to the invention is carried out with radioactive elements or with nonradioactive molecules. Among the radioactive isotopes used, mention may be made of 32P, 33P, 35S or 3H. The nonradioactive entities are selected from ligands such as biotin, avidin, streptavidin or digoxigenin, haptenes, dyes, and luminescent agents such as radioluminescent, chemoluminescent, bioluminescent, fluorescent or phosphorescent agents.

Nucleic acids can be obtained from the cells using known techniques. Nucleic acid herein refers to RNA, including mRNA, and DNA, including cDNA. The nucleic acid can be double-stranded or single-stranded (i.e., a sense or an antisense single strand) and can be complementary to a nucleic acid encoding a polypeptide. The nucleic acid content may also be an RNA or DNA extraction performed on a biological sample, including a biological fluid and fresh or fixed tissue sample.

There are many methods known in the art for the detection and quantification of specific nucleic acid sequences and new methods are continually reported. A great majority of the known specific nucleic acid detection and quantification methods utilize nucleic acid probes in specific hybridization reactions. Preferably, the detection of hybridization to the duplex form is a Southern blot technique. In the Southern blot technique, a nucleic acid sample is separated in an agarose gel based on size (molecular weight) and affixed to a membrane, denatured, and exposed to (admixed with) the labeled nucleic acid probe under hybridizing conditions. If the labeled nucleic acid probe forms a hybrid with the nucleic acid on the blot, the label is bound to the membrane.

In the Southern blot, the nucleic acid probe is preferably labeled with a tag. That tag can be a radioactive isotope, a fluorescent dye or the other well-known materials. Another type of process for the specific detection of nucleic acids in a biological sample known in the art are the hybridization methods as exemplified by U.S. Pat. No. 6,159,693 and U.S. Pat. No. 6,270,974, and related patents. To briefly summarize one of those methods, a nucleic acid probe of at least 10 nucleotides, preferably at least 15 nucleotides, more preferably at least 25 nucleotides, having a sequence complementary to a nucleic acid of interest is hybridized in a sample, subjected to depolymerizing conditions, and the sample is treated with an ATP/luciferase system, which will luminesce if the nucleic sequence is present. In quantitative Southern blotting, the level of the nucleic acid of interest can be compared with the level of a second nucleic acid of interest, and/or to one or more comparator control nucleic acids (e.g., positive control, negative control, quantity control, etc.).

Many methods useful for the detection and quantification of nucleic acid takes advantage of the polymerase chain reaction (PCR). The PCR process is well known in the art (U.S. Pat. No. 4,683,195, U.S. Pat. No. 4,683,202, and U.S. Pat. No. 4,800,159). To briefly summarize PCR, nucleic acid primers, complementary to opposite strands of a nucleic acid amplification target sequence, are permitted to anneal to the denatured sample. A DNA polymerase (typically heat stable) extends the DNA duplex from the hybridized primer. The process is repeated to amplify the nucleic acid target. If the nucleic acid primers do not hybridize to the sample, then there is no corresponding amplified PCR product. In this case, the PCR primer acts as a hybridization probe.

In PCR, the nucleic acid probe can be labeled with a tag as discussed elsewhere herein. Most preferably the detection of the duplex is done using at least one primer directed to the nucleic acid of interest. In yet another embodiment of PCR, the detection of the hybridized duplex comprises electrophoretic gel separation followed by dye-based visualization.

Typical hybridization and washing stringency conditions depend in part on the size (i.e., number of nucleotides in length) of the oligonucleotide probe, the base composition and monovalent and divalent cation concentrations (Ausubel et al., 1994, eds Current Protocols in Molecular Biology).

In a preferred embodiment, the process for determining the quantitative and qualitative profile of the nucleic acid of interest according to the present invention is characterized in that the amplifications are real-time amplifications performed using a labeled probe, preferably a labeled hydrolysis-probe, capable of specifically hybridizing in stringent conditions with a segment of the nucleic acid of interest. The labeled probe is capable of emitting a detectable signal every time each amplification cycle occurs, allowing the signal obtained for each cycle to be measured.

The real-time amplification, such as real-time PCR, is well known in the art, and the various known techniques will be employed in the best way for the implementation of the present process. These techniques are performed using various categories of probes, such as hydrolysis probes, hybridization adjacent probes, or molecular beacons. The techniques employing hydrolysis probes or molecular beacons are based on the use of a fluorescence quencher/reporter system, and the hybridization adjacent probes are based on the use of fluorescence acceptor/donor molecules.

Hydrolysis probes with a fluorescence quencher/reporter system are available in the market, and are for example commercialized by the Applied Biosystems group (USA). Many fluorescent dyes may be employed, such as FAM dyes (6-carboxy-fluorescein), or any other dye phosphoramidite reagents.

Among the stringent conditions applied for any one of the hydrolysis-probes of the present invention is the Tm, which is in the range of about 65° C. to 75° C. Preferably, the Tm for any one of the hydrolysis-probes of the present invention is in the range of about 67° C. to about 70° C. Most preferably, the Tm applied for any one of the hydrolysis-probes of the present invention is about 67° C.

In one aspect, the invention includes a primer that is complementary to a nucleic acid of interest, and more particularly the primer includes 12 or more contiguous nucleotides substantially complementary to the nucleic acid of interest. Preferably, a primer featured in the invention includes a nucleotide sequence sufficiently complementary to hybridize to a nucleic acid sequence of about 12 to 25 nucleotides. More preferably, the primer differs by no more than 1, 2, or 3 nucleotides from the target flanking nucleotide sequence in another aspect, the length of the primer can vary in length, preferably about 15 to 28 nucleotides in length (e.g., 16, 17, 18, 19, 20, 21, 22, 23, 24, 25, 26, or 27 nucleotides in length).

Kits

The present invention also pertains to kits useful in the methods of the invention. Such kits comprise various combinations of components useful in any of the methods described elsewhere herein, including for example, hybridization probes or primers (e.g., labeled probes or primers), antibodies, reagents for detection of labeled molecules, materials for the amplification of a subject's nucleic acids, a D-DT activator, a D-DT inhibitor, materials for quantitatively analyzing D-DT polypeptide or D-DT nucleic acid, materials for assessing the activity of a D-DT polypeptide or a D-DT nucleic acid, and instructional material. For example, in one embodiment, the kit comprises components useful for the quantification of D-DT nucleic acid in a biological sample obtained from a subject. In another embodiment, the kit comprises components useful for the quantification of D-DT polypeptide in a biological sample obtained from a subject. In a further embodiment, the kit comprises components useful for the assessment of the activity (e.g., enzymatic activity, receptor binding activity, etc.) of a D-DT polypeptide in a biological sample obtained from a subject.

In one embodiment, the kit comprises the components of a diagnostic assay for diagnosing infection, inflammatory disease, autoimmunity or cancer in a subject in need thereof, containing instructional material and the components for determining whether the level of D-DT is increased in a biological sample obtained from the subject. In various embodiments, determining whether the level of D-DT is increased in a biological sample obtained from the subject, the level of D-DT is compared with the level of at least one comparator control contained in the kit, such as a positive control, a negative control, a historical control, a historical norm, or the level of another reference molecule in the biological sample. In one embodiment, the reference molecule in the biological sample is MIF. In certain embodiments, the ratio of D-DT and MIF is determined to aid in the diagnosis.

In another embodiment, the kit comprises the components of a diagnostic assay for diagnosing ischemia-reperfusion injury in a subject in need thereof, containing instructional material and the components for determining whether the level of D-DT is reduced in a biological sample obtained from the subject. In various embodiments, determining whether the level of D-DT is reduced in a biological sample obtained from the subject, the level of D-DT is compared with the level of at least one comparator control contained in the kit, such as a positive control, a negative control, a historical control, a historical norm, or the level of another reference molecule in the biological sample. In one embodiment, the reference molecule in the biological sample is MIF. In certain embodiments, the ratio of D-DT and MIF is determined to aid in the diagnosis.

In a further embodiment, the kit comprises the components of an assay for monitoring the effectiveness of a treatment administered to a subject in need thereof, containing instructional material and the components for determining whether the level of D-DT in a biological sample obtained from the subject is modulated during or after administration of the treatment. In various embodiments, to determine whether the level of D-DT is modulated in a biological sample obtained from the subject, the level of D-DT is compared with the level of at least one comparator control contained in the kit, such as a positive control, a negative control, a historical control, a historical norm, or the level of another reference molecule in the biological sample. In one embodiment, the reference molecule in the biological sample is MIF. In certain embodiments, the ratio of D-DT and MIF is determined to aid in the monitoring of the treatment.

Therapeutic Inhibitor Compositions and Methods

In various embodiments, the present invention includes D-DT inhibitor compositions and methods of treating infection, inflammatory disease, autoimmunity and cancer. In various embodiments, the D-DT inhibitor compositions and methods of treatment of the invention diminish the amount of D-DT polypeptide, the amount of D-DT mRNA, the amount of D-DT enzymatic activity, the amount of D-DT receptor binding activity, or a combination thereof.

It will be understood by one skilled in the art, based upon the disclosure provided herein, that a decrease in the level of D-DT encompasses the decrease in D-DT expression, including transcription, translation, or both. The skilled artisan will also appreciate, once armed with the teachings of the present invention, that a decrease in the level of D-DT includes a decrease in D-DT activity (e.g., enzymatic activity, receptor binding activity, etc.). Thus, decreasing the level or activity of D-DT includes, but is not limited to, decreasing transcription, translation, or both, of a nucleic acid encoding D-DT; and it also includes decreasing any activity of a D-DT polypeptide as well. The D-DT inhibitor compositions and methods of the invention can selectively inhibit D-DT, or can inhibit both D-DT and MIF.

Inhibition of D-DT can be assessed using a wide variety of methods, including those disclosed herein, as well as methods known in the art or to be developed in the future. That is, the mutineer would appreciate, based upon the disclosure provided herein, that decreasing the level or activity of D-DT can be readily assessed using methods that assess the level of a nucleic acid encoding D-DT (e.g., mRNA), the level of a D-DT polypeptide present in a biological sample, the level of D-DT activity (e.g., enzymatic activity, receptor binding activity), or combinations thereof.

One skilled in the art, based upon the disclosure provided herein, would understand that the invention is useful in treating infection, inflammatory disease, autoimmunity or cancer in a subject in need thereof, whether or not the subject also being treated with other medication or therapy. Further, the skilled artisan would further appreciate, based upon the teachings provided herein, that the infection, inflammatory disease, autoimmunity or cancer treatable by the compositions and methods described herein encompass any pathology associated infection, inflammatory disease, autoimmunity or cancer where D-DT plays a role.

The D-DT inhibitor compositions and methods of the invention that decrease the level, enzymatic activity, or receptor binding activity of D-DT include, but should not be construed as being limited to, a chemical compound, a protein, a peptide, a peptidomemetic, an antibody, a ribozyme, a small molecule chemical compound, an antisense nucleic acid molecule (e.g., siRNA, miRNA, etc.), or combinations thereof. One of skill in the art would readily appreciate, based on the disclosure provided herein, that a D-DT inhibitor composition encompasses a chemical compound that decreases the level or activity of D-DT. Additionally, a D-DT inhibitor composition encompasses a chemically modified compound, and derivatives, as is well known to one of skill in the chemical arts. In a particular embodiment, the D-DT inhibitor is an siRNA comprising the nucleic acid sequence 5'-GCATGAC-CCTGTTGATGAA-3' (SEQ ID NO: 2).

The D-DT inhibitor compositions and methods of the invention that decrease the level or activity of D-DT include antibodies. The antibodies of the invention include a variety of forms of antibodies including, for example, polyclonal antibodies, monoclonal antibodies, intracellular antibodies ("intrabodies"), Fv, Fab and F(ab)$_2$, single chain antibodies (scFv), heavy chain antibodies (such as camelid antibodies), synthetic antibodies, chimeric antibodies, and humanized antibodies. In one embodiment, the antibody of the invention is an antibody that specifically binds to D-DT, and does not substantially bind to MIF. In another embodiment, the antibody of the invention is an antibody that specifically binds to D-DT, and also specifically binds to MIF. In a further embodiment, the antibody of the invention is a dual-specific antibody that concurrently binds both D-DT and MIF.

Further, one of skill in the art would, when equipped with this disclosure and the methods exemplified herein, appreciate that a D-DT inhibitor composition includes such inhibitors as discovered in the future, as can be identified by well-known criteria in the art of pharmacology, such as the physiological results of inhibition of D-DT as described in detail herein and/or as known in the art. Therefore, the present invention is not limited in any way to any particular D-DT inhibitor composition as exemplified or disclosed herein; rather, the invention encompasses those inhibitor compositions that would be understood by the routineer to be useful as are known in the art and as are discovered in the future.

Further methods of identifying and producing D-DT inhibitor compositions are well known to those of ordinary skill in the art, including, but not limited, obtaining an inhibitor from a naturally occurring source (i.e., *Streptomyces* sp., *Pseudomonas* sp., *Stylotella aurantium*). Alternatively, a D-DT inhibitor can be synthesized chemically. Further, the mutineer would appreciate, based upon the teachings provided herein, that a D-DT inhibitor composition can be obtained from a recombinant organism. Compositions and methods for chemically synthesizing D-DT inhibitors and for obtaining them from natural sources are well known in the art and are described in the art.

One of skill in the art will appreciate that an inhibitor can be administered as a small molecule chemical, a protein, an antibody, a nucleic acid construct encoding a protein, an antisense nucleic acid, a nucleic acid construct encoding an antisense nucleic acid, or combinations thereof. Numerous vectors and other compositions and methods are well known for administering a protein or a nucleic acid construct encoding a protein to cells or tissues. Therefore, the invention includes a method of administering a protein or a nucleic acid encoding a protein that is an inhibitor of D-DT. (Sambrook et al., 2001, Molecular Cloning: A Laboratory Manual, Cold Spring Harbor Laboratory, New York; Ausubel et al., 1997, Current Protocols in Molecular Biology, John Wiley & Sons, New York).

One of skill in the art will realize that diminishing the amount or activity of a molecule that itself increases the amount or activity of D-DT can serve in the compositions and methods of the present invention to decrease the amount or activity of D-DT.

Antisense oligonucleotides are DNA or RNA molecules that are complementary to some portion of an RNA molecule. When present in a cell, antisense oligonucleotides hybridize to an existing RNA molecule and inhibit translation into a gene product. Inhibiting the expression of a gene using an antisense oligonucleotide is well known in the art (Marcus-Sekura, 1988, Anal. Biochem. 172:289), as are methods of expressing an antisense oligonucleotide in a cell (Inoue, U.S. Pat. No. 5,190,931). The methods of the invention include the use of an antisense oligonucleotide to diminish the amount of D-DT, or to diminish the amount of a molecule that causes an increase in the amount or activity of D-DT, thereby decreasing the amount or activity of D-DT.

Contemplated in the present invention are antisense oligonucleotides that are synthesized and provided to the cell by way of methods well known to those of ordinary skill in the art. As an example, an antisense oligonucleotide can be synthesized to be between about 10 and about 100, more preferably between about 15 and about 50 nucleotides long. The synthesis of nucleic acid molecules is well known in the art, as is the synthesis of modified antisense oligonucleotides to improve biological activity in comparison to unmodified antisense oligonucleotides (Tullis, 1991, U.S. Pat. No. 5,023,243).

Similarly, the expression of a gene may be inhibited by the hybridization of an antisense molecule to a promoter or other regulatory element of a gene, thereby affecting the transcription of the gene. Methods for the identification of a promoter or other regulatory element that interacts with a gene of interest are well known in the art, and include such methods as the yeast two hybrid system (Bartel and Fields, eds., In: The Yeast Two Hybrid System, Oxford University Press, Cary, N.C.).

Alternatively, inhibition of a gene expressing D-DT, or of a gene expressing a protein that increases the level or activity of D-DT, can be accomplished through the use of a ribozyme. Using ribozymes for inhibiting gene expression is well known to those of skill in the art (see, e.g., Cech et al., 1992, J. Biol. Chem. 267:17479; Hampel et al., 1989, Biochemistry 28: 4929; Altman et al., U.S. Pat. No. 5,168,053). Ribozymes are catalytic RNA molecules with the ability to cleave other single-stranded RNA molecules. Ribozymes are known to be sequence specific, and can therefore be modified to recognize a specific nucleotide sequence (Cech, 1988, J. Amer. Med, Assn. 260:3030), allowing the selective cleavage of specific mRNA molecules. Given the nucleotide sequence of the molecule, one of ordinary skill in the art could synthesize an antisense oligonucleotide or ribozyme without undue experimentation, provided with the disclosure and references incorporated herein.

One of skill in the art will appreciate that inhibitors of D-DT can be administered singly or in any combination. Further, D-DT inhibitors can be administered singly or in any combination in a temporal sense, in that they may be administered concurrently, or before, and/or after each other. One of ordinary skill in the art will appreciate, based on the disclosure provided herein, that D-DT inhibitor compositions can be used to treat infection, inflammatory disease, autoimmunity or cancer in a subject in need thereof, and that an inhibitor composition can be used alone or in any combination with another inhibitor to effect a therapeutic result.

In various embodiments, any of the inhibitors of D-DT of the invention described herein can be administered alone or in combination with other inhibitors of other molecules associated with infection, inflammatory disease, autoimmunity or cancer, such as, for example, MIF. In some embodiments, the D-DT inhibitors of the invention selectively inhibit D-DT and do not also inhibit MIF. In other embodiments, the D-DT inhibitors of the invention inhibit D-DT and also inhibit MIF.

It will be appreciated by one of skill in the art, when armed with the present disclosure including the methods detailed herein, that the invention is not limited to treatment of a disease or disorder that is already established. Particularly, the disease or disorder need not have manifested to the point of detriment to the subject; indeed, the disease or disorder need not be detected in a subject before treatment is administered. That is, significant disease or disorder does not have to occur before the present invention may provide benefit. Therefore, the present invention includes a method for preventing infection, inflammatory disease, autoimmunity or cancer in a subject, in that a D-DT inhibitor composition, as discussed previously elsewhere herein, can be administered to a subject prior to the onset of the infection, inflammatory disease, autoimmunity or cancer, thereby preventing the infection, inflammatory disease, autoimmunity or cancer. The preventive methods described herein also include the treatment of a subject that is in remission for the prevention of a recurrence of an infection, inflammatory disease, autoimmunity or cancer.

One of skill in the art, when aimed with the disclosure herein, would appreciate that the prevention of infection, inflammatory disease, autoimmunity or cancer encompasses administering to a subject a D-DT inhibitor composition as a preventative measure against infection, inflammatory disease, autoimmunity or cancer. As more fully discussed elsewhere herein, methods of decreasing the level or activity of D-DT encompass a wide plethora of techniques for decreasing not only D-DT activity, but also for decreasing expression of a nucleic acid encoding D-DT, including either a decrease in transcription, a decrease in translation, or both.

Additionally, as disclosed elsewhere herein, one skilled in the art would understand, once armed with the teaching provided herein, that the present invention encompasses a method of preventing a wide variety of diseases, disorders and pathologies where a decrease in expression and/or activity of D-DT mediates, treats or prevents the disease, disorder or pathology. Methods for assessing whether a disease relates to increased levels or activity of D-DT are known in the art. Further, the invention encompasses treatment or prevention of such diseases discovered in the future.

The invention encompasses administration of an inhibitor of D-DT to practice the methods of the invention; the skilled artisan would understand, based on the disclosure provided herein, how to formulate and administer the appropriate D-DT inhibitor to a subject. Indeed, the successful administration of the D-DT inhibitor has been reduced to practice as exemplified herein. However, the present invention is not limited to any particular method of administration or treatment regimen.

Therapeutic Activators and Methods

In various embodiments, the present invention includes D-DT activator compositions and methods of treating ischemia-reperfusion injury in a subject, a tissue, or an organ in need thereof. In various embodiments, the D-DT activator compositions and methods of treatment of the invention increase the amount of D-DT polypeptide, the amount of D-DT mRNA, the amount of D-DT enzymatic activity, the amount of D-DT receptor binding activity, or a combination thereof.

It will be understood by one skilled in the art, based upon the disclosure provided herein, that an increase in the level of D-DT encompasses the increase in D-DT expression, including transcription, translation, or both. The skilled artisan will also appreciate, once armed with the teachings of the present invention, that an increase in the level of D-DT includes an increase in D-DT activity (e.g., enzymatic activity, receptor binding activity, etc.). Thus, increasing the level or activity of D-DT includes, but is not limited to, increasing the amount of D-DT polypeptide, increasing transcription, translation, or both, of a nucleic acid encoding D-DT; and it also includes increasing any activity of a D-DT polypeptide as well. The D-DT activator compositions and methods of the invention can selectively activate D-DT, or can activate both D-DT and MIF.

Thus, the present invention relates to the prevention and treatment of ischemia-reperfusion injury by administration of a D-DT polypeptide, a recombinant D-DT polypeptide, an active D-DT polypeptide fragment, or an activator of D-DT expression or activity.

It is understood by one skilled in the art, that an increase in the level of D-DT encompasses the increase of D-DT protein expression. Additionally, the skilled artisan would appreciate, that an increase in the level of D-DT includes an increase in D-DT activity. Thus, increasing the level or activity of D-DT includes, but is not limited to, increasing transcription, translation, or both, of a nucleic acid encoding D-DT; and it also includes increasing any activity of D-DT as well.

Activation of D-DT can be assessed using a wide variety of methods, including those disclosed herein, as well as methods well-known in the art or to be developed in the future. That is, the routineer would appreciate, based upon the disclosure provided herein, that increasing the level or activity of D-DT can be readily assessed using methods that assess the level of a nucleic acid encoding D-DT (e.g., mRNA) and/or the level of D-DT polypeptide in a biological sample obtained from a subject.

One skilled in the art, based upon the disclosure provided herein, would understand that the invention is useful in ischemia-reperfusion injury in subjects who, in whole (e.g., systemically) or in part (e.g., locally, tissue, organ), are being or will be, exposed to less than adequate oxygen levels. Ischemia-reperfusion injury can occur through the loss of ventilation, as well as through the loss of circulation, to all or to part, of the subject's body. In one embodiment, the invention is useful in treating or preventing ischemia-reperfusion injury in a tissue or organ intended for transplantation. The skilled artisan will appreciate, based upon the teachings provided herein, that the ischemia-reperfusion injuries treatable by the compositions and methods described herein encompass any ischemia-reperfusion injury.

A D-DT activator can include, but should not be construed as being limited to, a chemical compound, a protein, a peptidomemetic, an antibody, a ribozyme, and an antisense nucleic acid molecule. One of skill in the art would readily appreciate, based on the disclosure provided herein, that a D-DT activator encompasses a chemical compound that increases the level, enzymatic activity, or receptor binding activity of D-DT. In some embodiments, the enzymatic activity is tautomerase activity. Additionally, a D-DT activator encompasses a chemically modified compound, and derivatives, as is well known to one of skill in the chemical arts.

In various embodiments, the present invention also includes D-DT activator compositions and methods of immunostimulation in a subject in need thereof. Immunostimulation is useful in a variety of settings where an increase in the immunoactivity is desirable. One such non-limiting example is the use of a D-DT activator composition to increase immunoactivity before, during or after vaccination. Another such non-limiting example is the use of D-DT activator composition to increase immunoactivity when the subject's immune response is otherwise inadequate. In various embodiments, the D-DT activator compositions and methods of immunostimulation of the invention increase the amount of D-DT polypeptide, the amount of D-DT mRNA, the amount of D-DT enzymatic activity, the amount of D-DT receptor binding activity, or a combination thereof.

It will be understood by one skilled in the art, based upon the disclosure provided herein, that an increase in the level of D-DT encompasses the increase in D-DT expression, including transcription, translation, or both. The skilled artisan will also appreciate, once armed with the teachings of the present invention, that an increase in the level of D-DT includes an increase in D-DT activity (e.g., enzymatic activity, receptor binding activity, etc.). Thus, increasing the level or activity of D-DT includes, but is not limited to, increasing the amount of D-DT polypeptide, increasing transcription, translation, or both, of a nucleic acid encoding D-DT; and it also includes increasing any activity of a D-DT polypeptide as well. The D-DT activator compositions and methods of the invention can selectively activate D-DT, or can activate both D-DT and MIF. Thus, the present invention relates to immunostimulation by administration of a D-DT polypeptide, a recombinant D-DT polypeptide, an active D-DT polypeptide fragment, or an activator of D-DT expression or activity.

Further, one of skill in the art would, when equipped with this disclosure and the methods exemplified herein, appreciate that a D-DT activator includes such activators as discovered in the future, as can be identified by well-known criteria in the art of pharmacology, such as the physiological results of activation of D-DT as described in detail herein and/or as known in the art. Therefore, the present invention is not limited in any way to any particular D-DT activator as exemplified or disclosed herein; rather, the invention encompasses those activators that would be understood by the routineer to be useful as are known in the art and as are discovered in the future.

Further methods of identifying and producing a D-DT activator are well known to those of ordinary skill in the art, including, but not limited, obtaining an activator from a naturally occurring source (i.e., *Streptomyces* sp., *Pseudomonas* sp., *Stylotella aurantium*). Alternatively, a D-DT activator can be synthesized chemically. Further, the routineer would appreciate, based upon the teachings provided herein, that a D-DT activator can be obtained from a recombinant organism. Compositions and methods for chemically synthesizing D-DT activators and for obtaining them from natural sources are well known in the art and are described in the art.

One of skill in the art will appreciate that an activator can be administered as a small molecule chemical, a protein, a nucleic acid construct encoding a protein, or combinations thereof. Numerous vectors and other compositions and methods are well known for administering a protein or a nucleic acid construct encoding a protein to cells or tissues. Therefore, the invention includes a method of administering a protein or a nucleic acid encoding an protein that is an activator of D-DT. (Sambrook et al., 1989, Molecular Cloning: A Laboratory Manual, Cold Spring Harbor Laboratory, New York; Ausubel et al., 1997, Current Protocols in Molecular Biology, John Wiley & Sons, New York).

One of skill in the art will realize that diminishing the amount or activity of a molecule that itself diminishes the amount or activity of D-DT can serve to increase the amount or activity of D-DT. Antisense oligonucleotides are DNA or RNA molecules that are complementary to some portion of a mRNA molecule. When present in a cell, antisense oligonucleotides hybridize to an existing mRNA molecule and inhibit translation into a gene product. Inhibiting the expression of a gene using an antisense oligonucleotide is well known in the art (Marcus-Sekura, 1988, Anal. Biochem. 172: 289), as are methods of expressing an antisense oligonucleotide in a cell (Inoue, U.S. Pat. No. 5,190,931). The methods of the invention include the use of antisense oligonucleotide to diminish the amount of a molecule that causes a decrease in the amount or activity D-DT, thereby increasing the amount or activity of D-DT. Contemplated in the present invention are antisense oligonucleotides that are synthesized and provided to the cell by way of methods well known to those of ordinary skill in the art. As an example, an antisense oligonucleotide can be synthesized to be between about 10 and about 100, more preferably between about 15 and about 50 nucleotides long. The synthesis of nucleic acid molecules is well known in the art, as is the synthesis of modified antisense oligonucleotides to improve biological activity in comparison to unmodified antisense oligonucleotides 1991, U.S. Pat. No. 5,023,243).

Similarly, the expression of a gene may be inhibited by the hybridization of an antisense molecule to a promoter or other regulatory element of a gene, thereby affecting the transcription of the gene. Methods for the identification of a promoter or other regulatory element that interacts with a gene of interest are well known in the art, and include such methods as the yeast two hybrid system (Bartel and Fields, eds., In: The Yeast Two Hybrid System, Oxford University Press, Cary, N.C.).

Alternatively, inhibition of a gene expressing a protein that diminishes the level or activity of D-DT can be accomplished through the use of a ribozyme. Using ribozymes for inhibiting gene expression is well known to those of skill in the art (see, e.g., Cech et al., 1992, J. Biol. Chem. 267:17479; Hampel et al., 1989, Biochemistry 28: 4929; Altman et al., U.S. Pat. No. 5,168,053). Ribozymes are catalytic RNA molecules with the ability to cleave other single-stranded RNA molecules. Ribozymes are known to be sequence specific, and can therefore be modified to recognize a specific nucleotide sequence (Cech, 1988, J. Amer. Med. Assn, 260:3030), allowing the selective cleavage of specific mRNA molecules. Given the nucleotide sequence of the molecule, one of ordinary skill in the art could synthesize an antisense oligonucleotide or ribozyme without undue experimentation, provided with the disclosure and references incorporated herein.

One of skill in the art will appreciate that a D-DT polypeptide, a recombinant D-DT polypeptide, or an active D-DT polypeptide fragment can be administered singly or in any combination thereof. Further, a D-DT polypeptide, a recombinant D-DT polypeptide, or an active D-DT polypeptide fragment can be administered singly or in any combination thereof in a temporal sense, in that they may be administered simultaneously, before, and/or after each other. One of ordinary skill in the art will appreciate, based on the disclosure provided herein, that a D-DT polypeptide, a recombinant D-DT polypeptide, or an active D-DT polypeptide fragment can be used to prevent or treat ischemia-reperfusion injury, and that an activator can be used alone or in any combination with another D-DT polypeptide, recombinant D-DT polypeptide, active D-DT polypeptide fragment, or D-DT activator to effect a therapeutic result.

One of skill in the art will also appreciate that activators of D-DT gene expression can be administered singly or in any combination thereof. Further, D-DT activators can be administered singly or in any combination thereof in a temporal sense, in that they may be administered simultaneously, before, and/or after each other. One of ordinary skill in the art will appreciate, based on the disclosure provided herein, that D-DT activators can be used to prevent or treat ischemia-reperfusion injury, and that an activator can be used alone or in any combination with another activator, D-DT polypeptide, recombinant D-DT polypeptide, or active D-DT polypeptide fragment to effect a therapeutic result.

It will be appreciated by one of skill in the art, when armed with the present disclosure including the methods detailed herein, that the invention is not limited to treatment of ischemia-reperfusion injury once the ischemia-reperfusion injury is established. Particularly, the symptoms of the ischemia-reperfusion injury need not have manifested to the point of detriment to the subject; indeed, the ischemia-reperfusion injury need not be detected in a subject before treatment is administered. That is, significant pathology from an ischemia-reperfusion injury does not have to occur before the present invention may provide benefit. Therefore, the present invention, as described more fully herein, includes a method for preventing ischemia-reperfusion injury in a subject, in that a D-DT molecule, or a D-DT activator, as discussed elsewhere herein, can be administered to a subject prior to the onset of an ischemia-reperfusion injury, thereby preventing the ischemia-reperfusion injury.

One of skill in the art, when armed with the disclosure herein, would appreciate that the prevention of ischemia-reperfusion injury encompasses administering to a subject a D-DT polypeptide, a recombinant D-DT polypeptide, an active D-DT polypeptide fragment, or D-DT activator as a preventative measure against ischemia-reperfusion injury. As more fully discussed elsewhere herein, methods of increasing the level or activity of a D-DT encompass a wide plethora of techniques for increasing not only D-DT activity, but also for increasing expression of a nucleic acid encoding D-DT. Additionally, as disclosed elsewhere herein, one skilled in the art would understand, once armed with the teaching provided herein, that the present invention encompasses a method of preventing a wide variety of diseases where increased expression and/or activity of D-DT mediates, treats or prevents the disease. Further, the invention encompasses treatment or prevention of such diseases discovered in the future.

The invention encompasses administration of a D-DT polypeptide, a recombinant D-DT polypeptide, an active D-DT polypeptide fragment, or a D-DT activator to practice the methods of the invention; the skilled artisan would understand, based on the disclosure provided herein, how to formulate and administer the appropriate D-DT polypeptide, recombinant D-DT polypeptide, active D-DT polypeptide fragment, or D-DT activator to a subject. However, the present invention is not limited to any particular method of administration or treatment regimen. This is especially true where it would be appreciated by one skilled in the art, equipped with the disclosure provided herein, including the reduction to practice using an art-recognized model of ischemia-reperfusion injury, that methods of administering a D-DT polypeptide, a recombinant D-DT polypeptide, an active D-DT polypeptide fragment, or D-DT activator can be determined by one of skill in the pharmacological arts.

As used herein, the term "pharmaceutically-acceptable carrier" means a chemical composition with which an appropriate D-DT polypeptide, recombinant D-DT polypeptide, active D-DT polypeptide fragment, or D-DT activator, may be combined and which, following the combination, can be used to administer the appropriate D-DT polypeptide, recombinant D-DT polypeptide, active D-DT polypeptide fragment, or D-DT activator to a subject.

Pharmaceutical Compositions

Compositions identified as modulators of D-DT can be formulated and administered to a subject, as now described. For example, compositions identified as useful D-DT inhibitors for the treatment and/or prevention of infection, inflammatory disease, autoimmunity or cancer, can be formulated and administered to a subject, as now described. Further, compositions identified as useful D-DT activators, as well as D-DT polypeptides, recombinant D-DT polypeptides, and active D-DT polypeptide fragments, for the treatment and/or prevention of ischemia-reperfusion injury can be formulated and administered to a subject, as now described.

The invention encompasses the preparation and use of pharmaceutical compositions comprising a composition useful for the treatment of ischemia-reperfusion injury, or for the treatment of infection, inflammatory disease, autoimmunity or cancer, disclosed herein as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "pharmaceutically-acceptable carrier" means a chemical composition with which an appropriate D-DT modulator thereof, may be combined and which, following the combination, can be used to administer the appropriate D-DT modulator thereof, to a subject.

The pharmaceutical compositions useful for practicing the invention may be administered to deliver a dose of between about 0.1 ng/kg/day and 100 mg/kg/day.

In various embodiments, the pharmaceutical compositions useful in the methods of the invention may be administered, by way of example, systemically, parenterally, or topically, such as, in oral formulations, inhaled formulations, including solid or aerosol, and by topical or other similar formulations.

In addition to the appropriate therapeutic composition, such pharmaceutical compositions may contain pharmaceutically acceptable carriers and other ingredients known to enhance and facilitate drug administration. Other possible formulations, such as nanoparticles, liposomes, resealed erythrocytes, and immunologically based systems may also be used to administer an appropriate modulator thereof, according to the methods of the invention.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation.

Pharmaceutical compositions that are useful in the methods of the invention may be prepared, packaged, or sold in formulations suitable for oral, rectal, vaginal, parenteral, topical, pulmonary, intranasal, buccal, intravenous, ophthalmic, intrathecal and other known routes of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent.

Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, and hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e. such as with a physiologically degradable material), and methods of absorbing an aqueous or oily solution or suspension into an absorbent material, with or without subsequent drying.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, cutaneous, subcutaneous, intraperitoneal, intravenous, intramuscular, intracisternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions, Topically-administrable formulations may, for example, comprise from about 1% to about 10% (w/w) active ingredient, although the concentration of the active ingredient may be as high as the solubility limit of the active ingredient in the solvent Formulations for topical administration may further comprise one or more of the additional ingredients described herein.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares. Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, contain 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1-1.0% (w/w) solution or suspension of the active ingredient in an aqueous or oily liquid carrier. Such drops may further comprise buffering agents, salts, or one or more other of the additional ingredients described herein. Other opthalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, Remington's Pharmaceutical Sciences, Mack Publishing Co., Easton, Pa., which is incorporated herein by reference.

Typically dosages of the compound of the invention which may be administered to an animal, preferably a human, range in amount from about 0.01 mg to 20 about 100 g per kilogram of body weight of the animal. While the precise dosage administered will vary depending upon any number of factors, including, but not limited to, the type of animal and type of disease state being treated, the age of the animal and the route of administration. Preferably, the dosage of the compound will vary from about 1 mg to about 100 mg per kilogram of body weight of the animal. More preferably, the dosage will vary from about 1 µg to about 1 g per kilogram of body weight of the animal. The compound can be administered to an animal as frequently as several times daily, or it can be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc.

Methods of Identifying a D-DT Activators or D-DT Inhibitor

The current invention relates to a methods of identifying a compound that modulates the level of D-DT, the enzymatic activity of D-DT, the receptor binding activity of D-DT, or a combination thereof. In some embodiments, the method of identifying of the invention identifies a D-DT inhibitor compound that decreases the level of D-DT, the enzymatic activity of D-DT, the receptor binding activity of D-DT, or a combination thereof. In other embodiments, the method of identifying of the invention identifies a D-DT activator compound that increases the level of D-DT, the enzymatic activity of D-DT, the receptor binding activity of D-DT, or a combination thereof.

Other methods, as well as variation of the methods disclosed herein will be apparent from the description of this invention. In various embodiments, the test compound concentration in the screening assay can be fixed or varied. A single test compound, or a plurality of test compounds, can be tested at one time. Suitable test compounds that may be used include, but are not limited to, proteins, nucleic acids, antisense nucleic acids, small molecules, antibodies and peptides.

The invention relates to a method for screening test compounds to identify a modulator compound by its ability to modulate (i.e., increase or decrease) the level of D-DT, the enzymatic activity of D-DT, the receptor binding activity of D-DT, or a combination thereof by measuring the level of D-DT, the enzymatic activity of D-DT, the receptor binding activity of D-DT, or a combination thereof, in the presence and absence of the test compound.

The test compounds can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam et al., 1997, Anticancer Drug Des. 12:45).

Examples of methods for the synthesis of molecular libraries can be found in the art, for example, in: DeWitt et al., 1993, Proc. Natl. Acad. USA 90:6909; Erb et al., 1994, Proc. Natl. Acad. Sci. USA 91:11422; Zuckermann et al., 1994, J. Med. Chem. 37:2678; Cho et al., 1993, Science 261:1303; Carrell et al., 1994, Angew. Chem. Int. Ed. Engl. 33:2059; Carell et al., 1994, Angew, Chem. Int. Ed. Engl. 33:2061; and Gallop et al., 1994, J. Med. Chem. 37:1233.

Libraries of compounds may be presented in solution (e.g., Houghten, 1992, Biotechniques 13:412-421), or on beads (Lam, 1991, Nature 354:82-84), chips (Fodor, 1993, Nature 364:555-556), bacteria (Ladner U.S. Pat. No. 5,223,409), spores (Ladner U.S. Pat. No. '409), plasmids (Cull et al., 1992, Proc. Natl. Acad. Sci. USA 89:1865-1869) or on phage (Scott and Smith, 1990, Science 249:386-390; Devlin, 1990, Science 249:404-406: Cwirla et al., 1990, Proc. Natl. Acad. Sci. USA 87:6378-6382; Felici, 1991, J. Mol. Biol. 222:301-310; and Ladner supra).

In situations where "high-throughput" modalities are preferred, it is typical to that new chemical entities with useful properties are generated by identifying a chemical compound (called a "lead compound") with some desirable property or activity, creating variants of the lead compound, and evaluating the property and activity of those variant compounds.

In one embodiment, high throughput screening methods involve providing a library containing a large number of test compounds potentially having the desired activity. Such "combinatorial chemical libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments or the present invention, and are not to be construed as limiting in any way the remainder of the disclosure.

Example 1

The D-Dopachrome Tautomerase (D-DT) Gene Product is a Cytokine and Functional Homolog of Macrophage Migration Inhibitory Factor (MIF)

The functional characterization of human and mouse D-DT (also known as MIF-2) is described herein. Recombinant D-DT was produced and was demonstrated to bind with high affinity to CD74, activate the ERK1/2 MAP kinase signaling cascade, and recapitulate many of the inflammatory functions of MIF, including modulation of macrophage migration and glucocorticoidinduced immunosuppression. The administration of an anti-D-DT antibody, like anti-MIF, protects mice from lethal endotoxic shock by reducing the circulating levels of proinflammatory cytokines (TNF-α, IFN-γ, IL-12p70, and IL-1β) and increasing the circulating concentration of the anti-inflammatory cytokine, IL-10. An analysis of clinical samples from patients with sepsis or cancer also revealed that D-DT is systemically expressed and that circulating levels correlate with MIF and with the severity of inflammatory disease and malignancy.

Both mouse and human D-DT proteins show conservation in their catalytic, N-terminal proline but they lack MIF's —CXXC— and pseudo(E)LRmotifs, the latter of which is known to mediate noncognate interactions with CXCR2 and CXCR4 (Bernhagen, et al., 2007, Nat Med 13:587-596; Weber, et al., 2008, Proc Natl Acad Sci USA 105: 16278-16283). As described herein, a recombinant, endotoxin-free D-DT protein was produced and it is shown that D-DT, like MIF, tautomerizes the model substrate, p-hydroxyphenylpyruvate, albeit the measured velocity is ~10 times lower than that analyzed for MIF. D-DT is constitutively expressed in different tissues and it is up-regulated by proinflammatoty activation. MIF is known to bind to the type II transmembrane protein, CD74, leading to its intracellular phosphorylation, the recruitment of the coreceptor CD44, and the activation of SRC family kinases and the ERK1/2 MAPK pathway (Shi, et al., 2006 Immunity 25:595-606; Leng, et al., 2003, J Exp Med 197:1467-1476). Although the interaction between D-DT and sCD74 was reduced in comparison with MIF when measured by both competition binding and BIAcore studies, the ERK1/2 activation potential of D-DT and MIF appeared comparable by Western blotting. The KD of sCD74 for D-DT was 60% of that measured for MIF; D-DT was found to have an ~3-fold higher association rate (ka) to sCD74 but to dissociate (kd) ~11-fold faster than MIF. Although not wishing to be bound by any particular theory, these differences in association and dissociation values may differentiate the signaling action of the two proteins; e.g., D-DT binding to the receptor might not always trigger a signaling cascade but might result in its internalization. MIF showed a steeper dose response than D-DT in measurements of macrophage migration inhibition and glucocorticoid overriding, but the resolution of these cell-based assays may be too limited to make precise, quantitative conclusions. These results may support the notion that D-DT is a less potent cytokine that might be associated with the down-regulation of inflammation.

As described herein, anti-D-DT antibodies were produced that do not cross-react with MIF; these antibodies allowed for measurements of this protein in biologic specimens. D-DT was expressed in the serum of endotoxemic mice at levels that were ~60% those of MIF. MIF is a high, upstream mediator of septic shock, and immunoneutralization, genetic deletion, or pharmacologic inhibition of MIF protects from lethal shock induced by different microbial pathogens, even when administered many hours after microbial invasion (Bernhagen, et al., 1993, Nature 365:756-759; Bozza, et al., 1999, J Exp Med 189:341-346; Calandra, et al., 1998, Proc Natl Acad Sci USA 95:11383-11388; Mona, et al., 2007, J Clin Invest 117: 3059-3066; McDevitt, et al., 2006, J Exp Med 203:1185-1196). Immunoneutralization of D-DT conferred protection from lethal endotoxemia and this effect was accompanied by a broad reduction in the systemic expression of TNF-α, IL-1β, IL-12p70, and IFN-γ and an increase in the circulating levels of the anti-inflammatory mediator, IL-10. Given current development of MIF inhibitors for the treatment of the inflammatory diseases (Arjona, et al., 2007, J Clin Invest 117: 3059-3066; Lolis, et al., 2003, Nat Rev Drug Discov 2:635-645; Cournia, et al. 2009, J Med Chem 52:416-424), it was also of interest to determine whether the combined neutralization of MIF and D-DT had a synergistic effect. MIF levels are elevated in patients with systemic inflammatory disease or with neoplasia, and in many instances a correlation between disease severity and MIF levels has been observed (Grieb, et al., 2010, Drug News Perspect 23:257-264), Like MIF, D-DT circulates at baseline levels in healthy individuals and there is a correlation in the plasma concentrations of the two mediators. Circulating D-DT levels increase significantly in patients with sepsis or ovarian cancer and show a strong correlation with MW, consistent with the explanation that the two mediators may be coordinately expressed in response to similar activating stimuli. The findings described herein include that D-DT is a close structural and functional homolog of MIF, that it binds and activates the MW receptor, and that targeting D-DT, similar to MIF, protects mice from lethal endotoxemia.

Like MIF (Bather, et al., 1997, Am J Pathol 150:235-246), D-DT was found to be widely expressed in tissues. As described elsewhere herein, macrophages produce 20-fold more MIF than D-DT in response to LPS, consistent with the explanation that there may be cell-specific release of these mediators and that in contrast to MIF, nonmacrophage sources of D-DT contribute more importantly to the systemic expression of D-DT than MIF. Computational inspection of the D-DT and MIF promoter regions shows similarities in the presence of serum-responsive, SP-1 and AP-1 binding elements (alggen.lsi.upc.es). Of note, the human D-DT gene lacks the polymorphic, CATT5-8 microsatellite repeat that exists in the MIF promoter (rs5844572) and that regulates MIF expression and is associated with the severity of autoimmune inflammatory diseases (Grieb, et al., 2010, Drug News Perspect 23:257-264), Although not wishing to be bound by any particular theory, one difference between MIF and D-DT may lie in the allele-specific regulation of MIF expression but not D-DT. At the protein level, D-DT lacks MIF's pseudo(E)LR domain, which is necessary for activation of CXCR2. Bernhagen and colleagues have reported that MIF initiates coordinated receptor interactions between CD74 and CXCR2/CXCR4 (Bernhagen, et al., 2007, Nat Med 13:587-596; Weber, et al., 2008, Proc Natl Acad Sci USA 105: 16278-16283). D-DT's high binding affinity to CD74 also may facilitate direct chemotactic effects, perhaps in concert with MIF or IL-8, which is expressed upon CD74 signaling (Coleman, et al., 2008, J Immunol 181:2330-2337; Binsky, et al., 2007, Proc Natl Acad Sci USA 104:13408-13413). D-DT binds the intracellular protein, JAB1, indicating that it might affect the regulation of cell cycle control and signalosoine function, similarly to MIF (Kleemann, et al., 2000, Nature 408:211-216). Like MIF, D-DT lacks an N-terminal signal sequence and it may be produced in sufficient intracytoplasmic concentrations to influence these regulatory pathways. In summary, the data disclosed herein identify D-DT to be a cytokine and a close functional homolog of MIF.

The data described herein support the targeting of D-DT, as well as the simultaneous targeting of D-DT and MIF, in various diseases and disease models.

The materials and methods employed in this example are now described.

Cloning and Purification of D-DT Protein

The cDNAs for the human and mouse D-DT proteins were prepared by amplification of mRNA from human or murine monocytes and subcloned into the pET22b expression vector. For native protein expression, a stop codon was engineered. Bacterial extract was purified using a Q Sepharose column (Amersham) and subsequent HPLC using a C18 column (Amersham). D-DT was refolded using the protocol established for MIF renaturation (Bernhagen, et al., 1994, Biochemistry 33: 14144-14155). Protein purity was verified by Coomassie and fidelity confirmed by mass spectroscopy. The resulting proteins contained <1 pg LPS/μg protein as quantified by the PyroGene Recombinant Factor C assay (Cambrex). MIF proteins were produced as described earlier (Bernhagen, et al., 1994, Biochemistry 33: 14144-14155). D-dopachrome tautomerase activity was assessed using the substrate HPP, measuring the change in absorbance at 306 nm for 180 s (Stamps, et al., Biochemistry 39:9671-9678).

Anti-D-DT Antibody and ELISA

Polyclonal antibodies against recombinant mouse or human D-DT were produced in rabbits. IgG antibody fractions were isolated by Protein A agarose affinity chromatography (Pierce) and sterile filtered. Microliter plates (Nunc) were coated with 15 μg/mL of polyclonal anti-D-DT, washed, and blocked in 1% BSA and 1% sucrose. Samples were added and incubated for 2 hours, followed by biotinylated anti-D-DT antibody and a streptavidin-HRP conjugate. The D-DT concentrations were calculated by extrapolation from a sigmoidal quadratic standard curve using native D-DT protein (dynamic range, 0-625 pg/mL). For mouse or human D-DT, the detection limit was 15 pg/mL.

MIF Receptor Binding Studies

Binding of D-DT to the MIF receptor, CD74, was studied by competition binding assay as described previously (Leng, et al., 2003, J Exp Med 197:1467-1476). Real-time binding interaction of MIF or D-DT with CD7473-232 was measured by surface plasmon resonance using a BIAcore 2000 optical biosensor (Kamir, et al., 2008, J Immunol 180:8250-8261). The MIF receptor sCD74 was immobilized to the chip, and binding of the ligands D-DT and MIF was measured in five serial dilutions, three times for each dilution sample. Sensorgram response data were analyzed in the BIA evaluation kinetics package and the equilibrium binding constants calculated in the same experiment.

D-DT Protein Expression in Murine Tissues

Tissues were isolated from C57BL/6 mice, and proteins were analyzed by Western blot (Bacher, et al., 1997, Am J Pathol 150:235-246). For immunohistochemistry, tissue sections from C57BL/6 mice (Mizue, et al., 2005, Proc Natl Acad Sci USA 102:14410-14415) were deparaffinized and antigen retrieval was performed using the Target Retrieval Solution (Dako). The specificity of anti-D-DT antibody staining was established by preabsorbing an aliquot of the antibody with a 1,000-fold molar excess of either D-DT or MIF. Slides were incubated with rabbit anti-D-DT or IgG control antibody (1:50) overnight and visualized with the Liquid DAB+Substrate Chromogen System (Dako). To allow a semiquantitative comparison of different tissues, all slides were developed for 10 min.

siRNA-Mediated Knockdown of D-DT and MIF

Immortalized murine macrophages (Duewell, et al., 2010, Nature 464:1357-1361) were transfected with 50 nM siRNA using HiPerFect (Qiagen). Sequences used were 5'-TCAAC-TATTACGACATGAA-3: (SEQ ID NO: 1) for MIF and 5'-GCATGACCCTGTTGATGAA-3'(SEQ ID NO: 2) for D-DT.

Signal Transduction Studies

Mouse peritoneal macrophages ($1 \times 10^6$/well) were rendered quiescent by incubation in 0.1% FBS before stimulation with D-DT or MIF for 2 hours (Mitchell, et al., 1999, J Biol Chem 274:18100-18106). Cells were lysed in RIPA buffer and lysates were run on a 4-12% Bis-Tris NuPage gel (Invitrogen). Immunoblotting was conducted with Abs directed against total ERK1/2, and phospho-ERK-1/2 (Cell Signaling).

Migration and Glucocorticoid Overriding Assays

Migration assays were performed as described previously (Hermanowski-Vosatka, et al., 1999, Biochemistry 38:12841-12849). Briefly, human monocytes were incubated for 20 min with MIF or D-DT. Media with or without 25 ng/mL MCP-1 was added in the lower compartment of migration chambers and monocytes was added to the transwell (0.5-μm pore size) for 90 min. Cells from the lower migration chamber were lysed, and DNA was fluorescently labeled and enumerated at 480/520 nm. Following the original glucocorticoid overriding methodology of Calandra et al. (Calandra, et al., 1995, Nature 377:68-71), macrophages were preincubated for 1 hour with 100 nM dexamethasone (Sigma) and MIF or D-DT before adding 100 ng/mL LPS (Sigma). TNF levels in supernatants were measured by ELISA (eBioscience).

MIF/JAB1 Communoprecipitation

Mif−/−MEFs were lysed in ice-cold buffer and incubated with MIF or D-DT, respectively (Kleemann, et al., 2000, Nature 408:211-216). Two micrograms of anti-JAB1

(2A10.8; Gene Tex/Biozol) or IgG1 control was added and the protein complexes were pulled down with magnetic protein G beads (Invitrogen). Blotted proteins were visualized using an anti-MIF or anti-D-DT antibodies and then reprobed with anti-JAB1 antibody.

Endotoxemia Model.

Endotoxemia was induced in female BALB/c mice (8 wk old) by i.p. administration of *E. coli* LPS 0111:B4 (Sigma) at a dose of 12.5 mg/kg for serum cytokine measurement and 20 mg/kg for intervention experiments (LD80). For D-DT neutralization studies, mice were injected i.p. with 200 µL of rabbit anti-D-DT antiserum or nonimmune serum 2 hours before administration of LPS. Mice were monitored every 4 hours within the first 72 hours and then twice daily until death or until 14 days. Cytokine levels were obtained by bleeding mice 4, 24, and 36 hours after LPS challenge, and serum cytokines were analyzed by Luminex (Bio-Rad).

Patient Samples

Serum concentrations of D-DT and MIF were measured in 85 healthy individuals and in 37 septic patients hospitalized in the medical intensive care unit (Lesur, et al., 2010, Crit Care 14:R131). The median APACHE II score at the time of intensive care unit admission was 22 points (range: 10-36 points). The mortality rate was 27%. The etiologic agents of sepsis were Gram-negative bacteria (43%) and Gram-positive bacteria (49%). Two patients had an infection with Grampositive and Gram-negative bacteria and one with fungi. Sera from women with biopsy-proven ovarian cancer (n=21) were from Yale—New Haven Hospital.

The results of this example are now described.

Purification and Characterization of the D-DT Protein

Figure 1B:
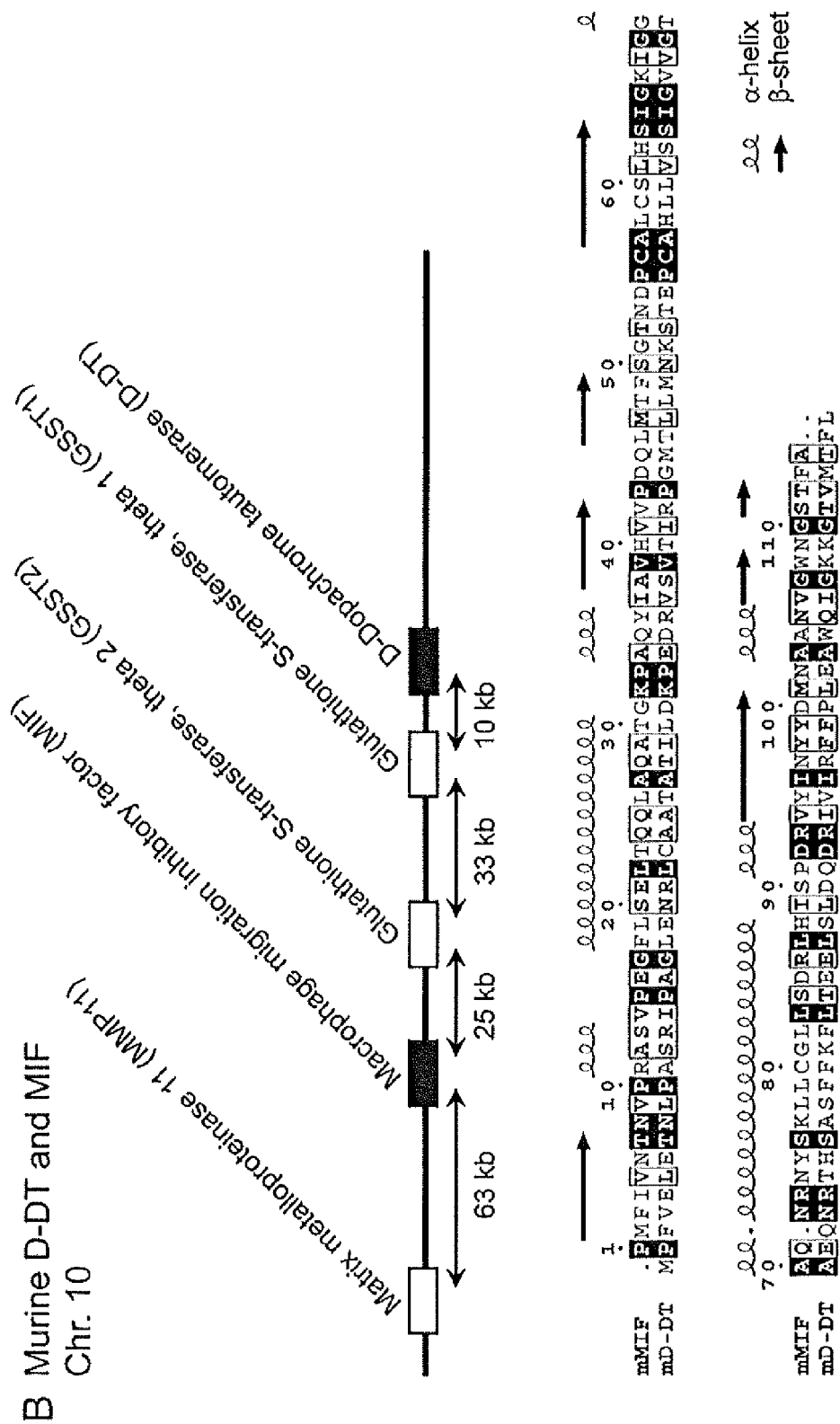

The genes for MIF and D-DT lie within 0.1 kb of each other in both the mouse and human genomes and have a similar organizational relationship with nearby genes for matrix metalloproteinase 11 and two theta class GSTs (FIG. 1). The amino acid sequences show 34% identity between human MIF and human D-DT and 27% identity between murine MW and murine D-DT. The D-DT proteins share with MW a canonical N-terminal proline (formed after posttranslational excision of the initiating methionine), which catalyzes substrate tautomerization (Bendrat, et al., 1997, Biochemistry 36:15356-15362), but they lack two of the three conserved cysteines (Cys59 and Cys80) that appear in all known mammalian MIF proteins. Murine and human D-DT also lack the pseudo(E)LR (Arg11, Asp44) motif that mediates MIF's non-canonical interactions with the CXCR2 chemokine receptor (Weber, et al., 2008, Proc Natl Acad Sci USA 105: 16278-16283). The mRNA for D-DT does not encode either an N-terminal or an internal secretory signal sequence, suggesting that like MIF, D-DT is secreted by a specialized, nonclassical export pathway (Merk, et al., 2009, J Immunol 182: 6896-6906).

Figure 2:
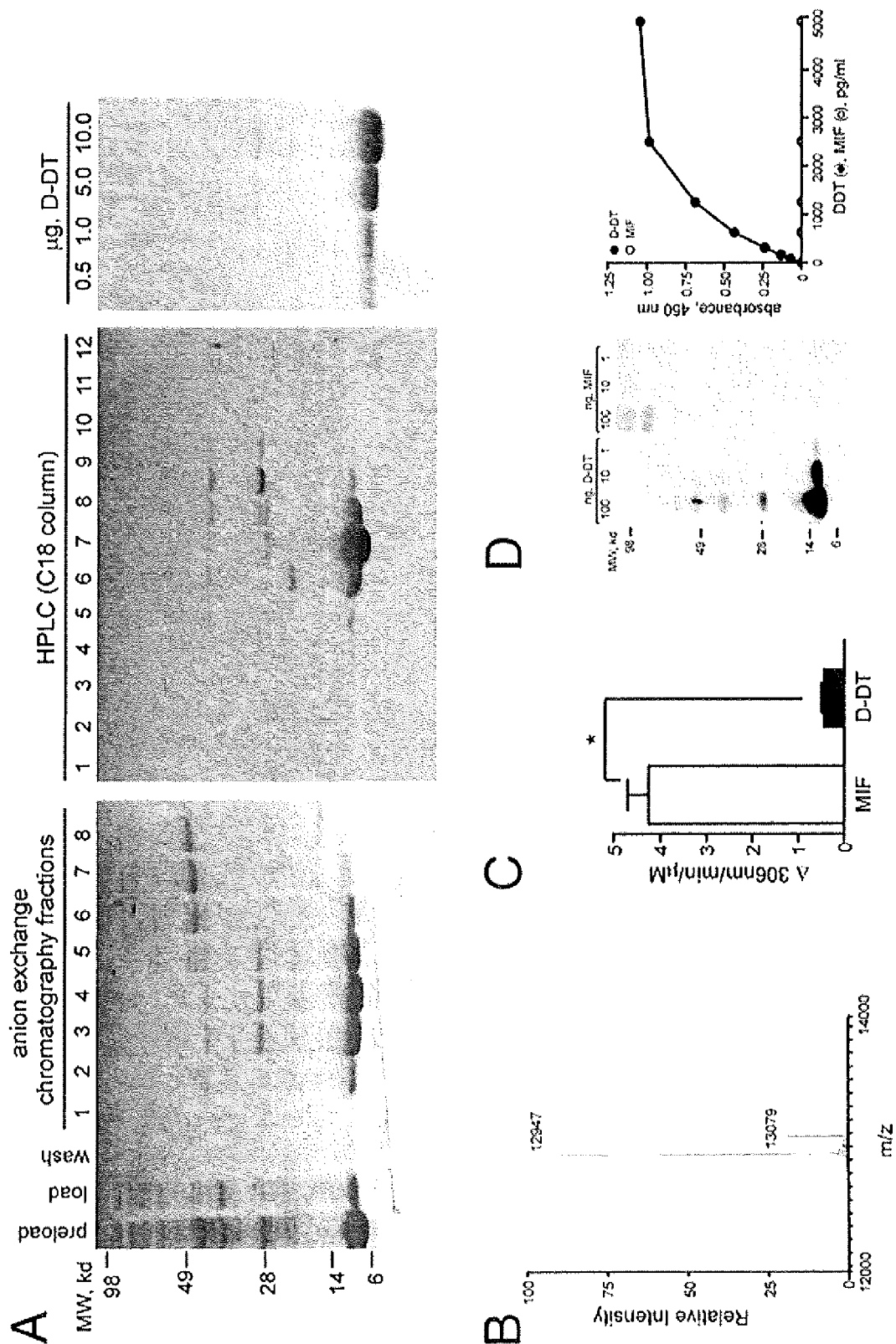
FIG. 2 depicts the results of experiments characterizing the D-DT protein. Characterization of the D-DT protein. (A) SDS/PAGE and Coomassie analysis of sequential purification steps of recombinant D-DT protein. The examples shown are for mouse D-DT but qualitatively identical results were obtained for human D-DT. (B) Electrospray ionization mass spectrometry of mouse D-DT showing a molecular mass (m/z) that is within 0.02% accuracy of the predicted m/z (12,946 Da). (C) Tautomerization activity of human MIF and D-DT measured with the substrate, p-hydroxyphenylpyruvate. Results are expressed as mean±SD of duplicate measurements and are representative of three experiments, (D) Anti-D-DT antibody specifically recognizes D-DT. (Left) Anti-D-DT antibody recognizes recombinant murine D-DT protein in Western blotting (1-100 ng/lane), but does not detect recombinant mouse MM. (Right) D-DT ELISA quantifies concentrations in the picogram range and shows no crossreactivity to MIF. Results are expressed as mean±SD of duplicate measurements and are representative for two independent experiments.

The cDNAs for human and mouse D-DT were prepared from monocytes and cloned into a bacterial expression vector for recombinant protein production. Work was performed with native sequence proteins because structure-function studies have shown that modifications of the N or C termini interfere with trimer formation, the functional unit of MIF (Bendrat, et al., 1997, Biochemistry 36:15356-15362; Sun, et al., 1996, Proc Natl Acad Sci USA 93: 5191-5196; El-Turk, et al., 2008, Biochemistry 47:10740-10756). Recombinant D-DT protein was purified by anion exchange chromatography followed by high performance liquid chromatography (HPLC) (FIG. 2A). Mass spectroscopy of purified mouse D-DT protein gave an m/z of 12,947, which lies within 0.02% of the calculated mass for D-DT (FIG. 2B). A minor peak of 13,079 Da also was detected; this peak corresponds to the molecular mass of D-DT with an uncleaved N-terminal methionine (expected m/z=13,077). MIF tautomerizes model substrates such as D-dopachrome and p-hydroxyphenylpyruvate (HPP) (whether a physiological substrate exists is unknown) (Fingerle-Rowson, et al., 2009, Mol Cell Biol 29:1922-1932), and D-DT purified from liver has tautomerization activity (Rosengren, et al., 1996, Mol Med 2:143-149; Odh, et al., 1993, Biochem Biophys Res Commun 197:619-624). It was verified that recombinant D-DT tautomerizes HPP with a specific activity that is ~10 times lower than that measured for MIF (D-DT=$0.5\pm0.1\Delta306\cdot min-1\cdot\mu M-1$, and MIF=$4.3\pm1.1\Delta306\cdot min-1\cdot\mu M-1$, P<0.001) (FIG. 2C). A possible explanation for the discrepancy inactivity might be structural differences in the active site regions of D-DT and MIF, resulting in a reduced affinity of D-DT to its substrate (Sugimoto, et al., 1999, Biochemistry 38:3268-3279; Sun, et al., 1996, Proc Natl Acad Sci USA 93: 5191-5196). A polyclonal anti-D-DT antibody was prepared to establish an ELISA. This antibody recognized both murine and human D-DT but did not cross-react with MIF in its denatured form (assessed by Western blot; FIG. 2D, Left) or in its native form (assessed by ELISA; FIG. 2D, Right).

D-DT Binds the MIF Receptor, CD74, and the Intracellular Protein, JAB1

Figures 3A, 3B:
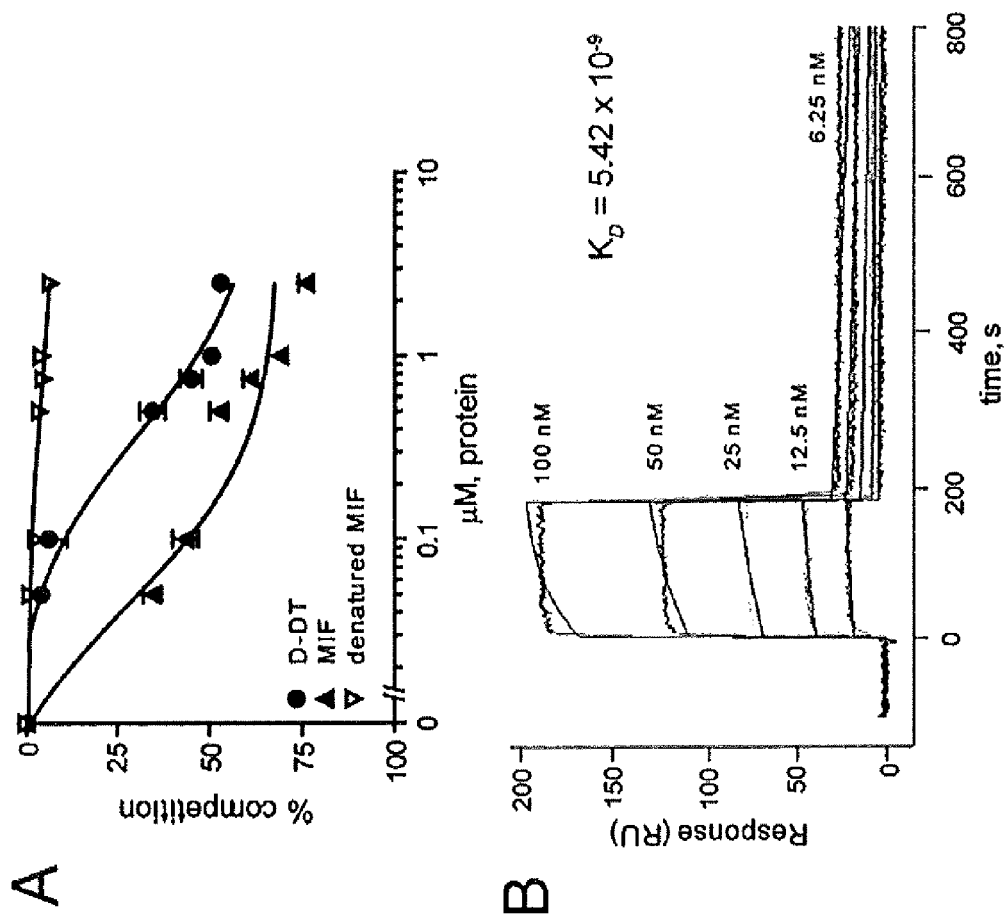
FIGS. 3A-3E, depicts the results of experiments demonstrating the D-DT binds with high affinity to the MIF receptor. D-DT binds with high affinity to the MIF receptor, CD74. (A) Concentration-dependent binding of D-DT and MIF to the MIF receptor ectodomain, sCD74, using biotinylated human MIF as competitor, Heat-denatured MIF served as a negative control. (B) Real-time surface plasmon resonance analysis (BTAcore) of the interaction between D-DT and sCD74. (C) Communoprecipitation of D-DT/JAB1 and MIF/JAB1. (Left) Cells were lysed and recombinant D-DT was added. JAB1/D-DT-containing protein complexes were coprecipitated by pull-down of JAB1, and D-DT was detected by Western blot. (Right) Communoprecipitation between JAB1 and MIF following the same protocol, (D) D-DT is differentially expressed in mouse tissue. Protein lysates (75 µg) were separated by SDS/PAGE and analyzed by Western blot for D-DT, MIF, and CD74 (n=2 mice studied). (E) D-DT protein expression analyzed by immunostaining of five representative organs from a C57BL/6 mouse (n=3 mice studied).
Figure 3C:
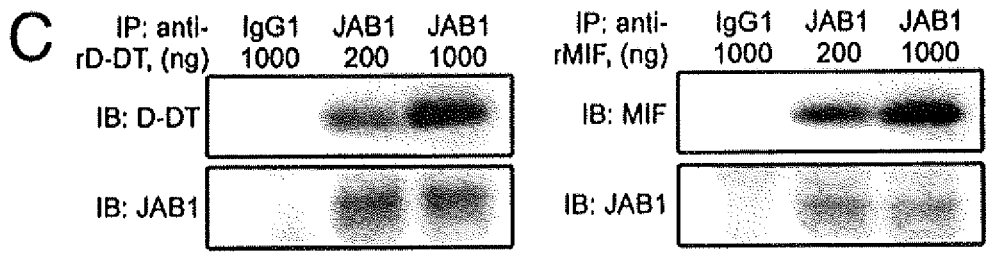

MIF activates ERK 1/2 phosphorylation by engaging CD74, and a high-affinity binding interaction between MW and the CD74 ectodomain (CD7473-232 or sCD74) has been demonstrated by surface plasmon resonance (Leng, et al., 2003, J Exp Med 197:1467-1476). The interaction between D-DT and sCD74 in a competition binding assay was studied. D-DT reduced MIF binding to the CD74 ectodomain in a dose-dependent manner, with a maximal effect of ~50% compared with MIF (FIG. 3A). Measurement of the equilibrium dissociation constants between human D-DT or MIF and sCD74 by surface plasmon resonance (BTAcore analysis) revealed a high-affinity binding interaction between D-DT and the MIF receptor (KD of $5.42\times10-9$ M) (FIG. 3B), albeit 60% lower than for MIF (KD=$1.40\times10-9$ M). Detailed analysis revealed a ka of $1.2\times105$ M-1·s-1 for D-DT and only $4.3\times104$ M-1·s-1 for MIF, whereas the dissociation rate (kd) was 11-fold lower for MIF than for D-DT ($6\times10-5$·s-1 and $6.6\times10-4$·s-1, respectively). These measurements demonstrate that D-DT has an ~3-fold higher binding rate to the receptor CD74, but also dissociates much faster than MIF. The intracellular transcriptional regulator and COP9 signalosome component JAB1 is a well characterized binding partner of MIF that has been implicated in MIF-dependent control of cell proliferation (Kleemann, et al., 2000, Nature 408: 211-216). D-DT binds to JAB1 as demonstrated by coimmunoprecipitation (FIG. 3C), and the interaction affinity between JAB1 and D-DT appears comparable to that observed between JAB1 and MIF.

Differential Expression of D-DT and MIF

Figure 3D:
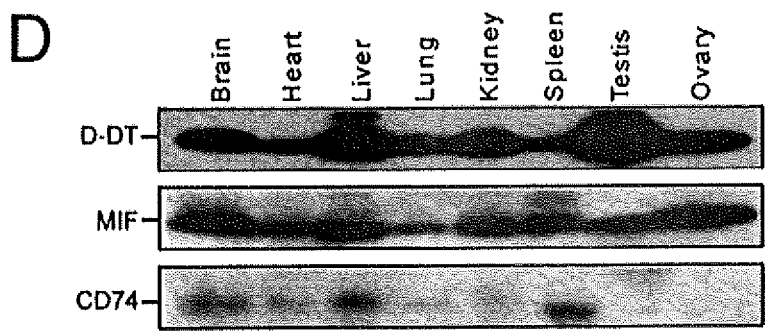
Figure 3E:
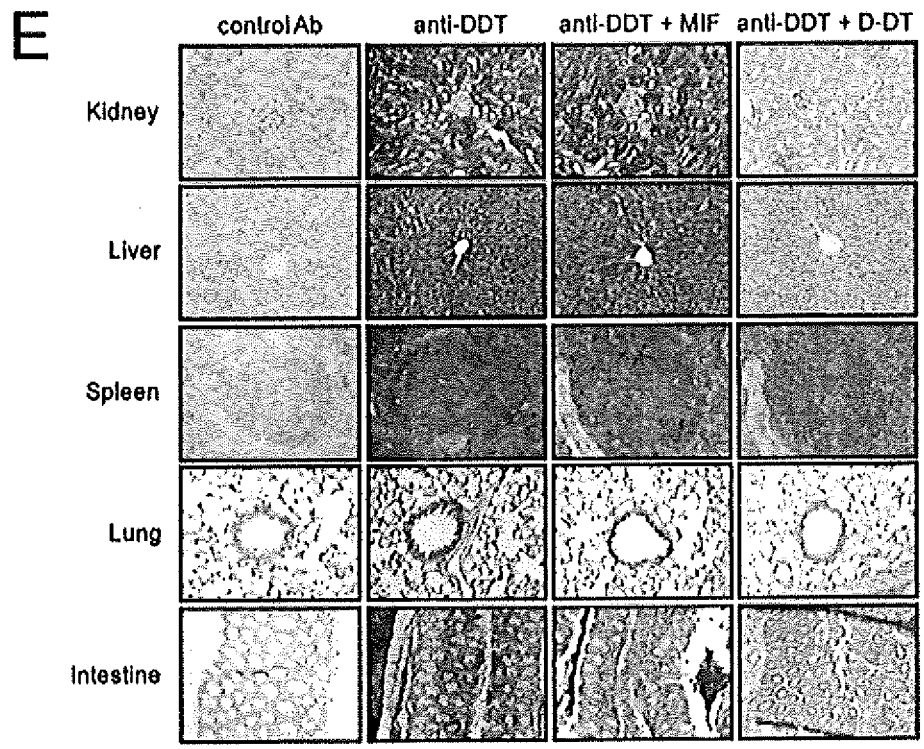

The differential expression of D-DT in tissue compared with MIF was assessed. Esumi et al. have published Northern blotting data for D-DT expression that suggest enhanced expression in the murine brain compared with Mif (Esumi, et al., 1998, Mamm Genome 9:753-757). Eight different mouse organs were analyzed by Western blotting for D-DT, MIF, and CD74. D-DT and MIF were present in constitutive and appreciable levels in all tissues examined, with the greatest difference observed in the testis, where D-DT appeared in several-fold higher concentrations compared with MIF (FIG. 3D). Immunostaining of murine tissue confirmed these results and showed that D-DT, like MIF (Bacher, et al., 1997, Am J Pathol 150:235-246), is detected in virtually all cells, with prominent staining in the epithelia of the kidney, the lung, the bowel, hepatocytes, and the follicular area of the spleen (FIG. 3E).

Figure 4A:
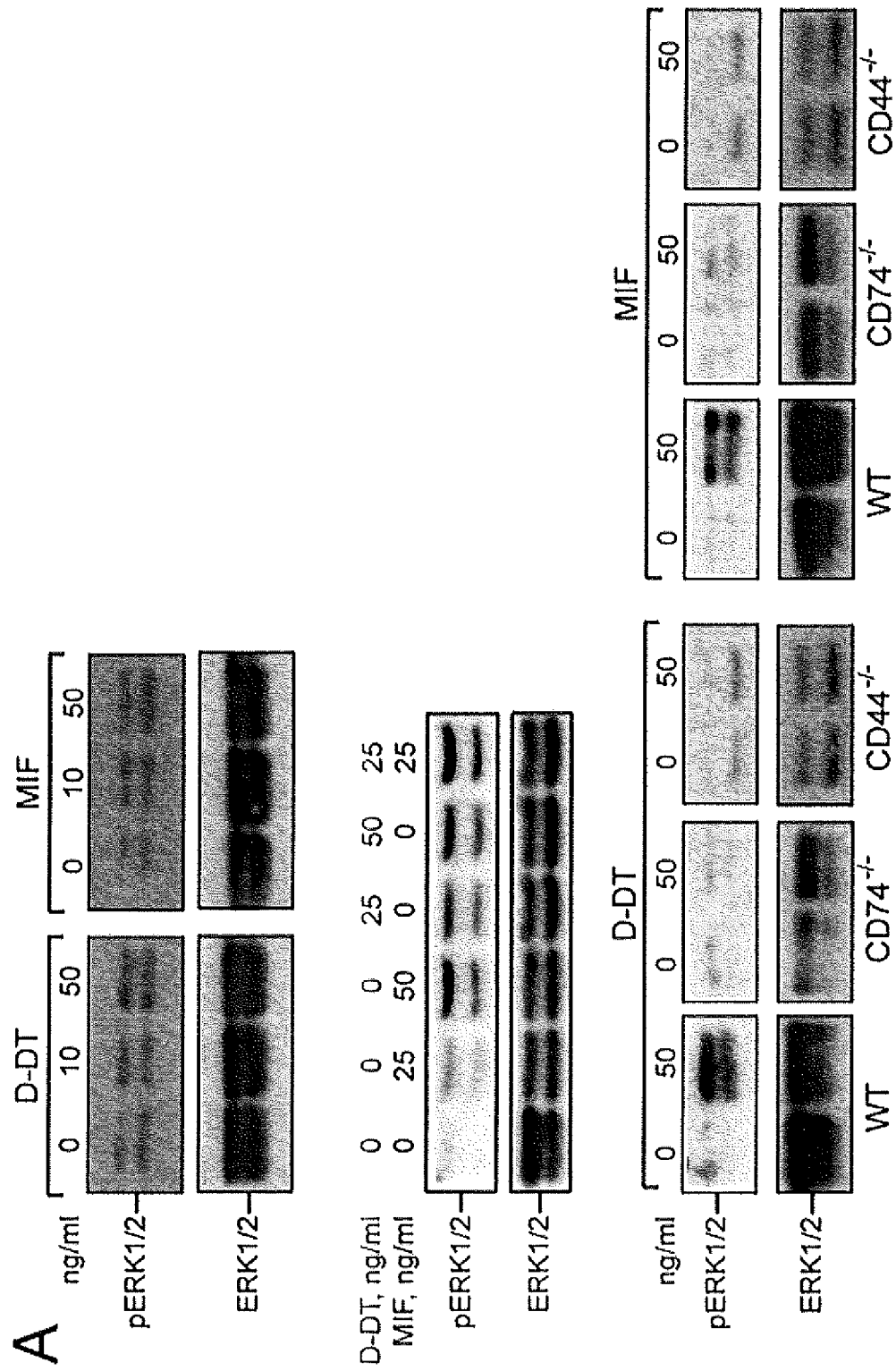
FIGS. 4A-4C, depicts the results of experiments assessing the functional comparison of D-DT and MIF. (A) D-DT activates the sustained ERK1/2 MAP kinase pathway in a MIF receptor complex (CD74/CD44)-dependent manner. (Top) Macrophages ($1 \times 10^6$/mL) were treated with 0, 10, or 50 ng/mL of D-DT or MIF for 2 hours. Cell lysates were analyzed for phosphorylation of ERK1/2. (Middle) Macrophages were treated with the indicated concentrations of D-DT, MW, or D-DT plus MIF. Lysates were analyzed for the phosphorylation status of ERK1/2. (Bottom) Wild-type and MIF receptor knockout (CD74-/- or CD44-/-) macrophages were treated with 50 ng/mL of D-DT or MIF for 2 hours, and cell lysates were analyzed by Western blot. Results are representative of at least two independent experiments. (B) Increasing concentrations of D-DT or MIF inhibit the chemotaxis of human peripheral blood monocytes to MCP-1. Data shown are mean±SD of quadruplicate assays and statistical significance for the comparison of MIF vs. D-DT was analyzed by an unpaired Student's t test; *P<0.01. (C) D-DT or MIF inhibits glucocorticoid-mediated suppression of TNF production. Macrophages were preincubated for 1 hour with or without dexamethasone (Dex, 100 nM), MIF, or D-DT (100 ng/mL) and then stimulated with LPS (100 ng/mL). Supernatants were collected after 4 hours and TNF was quantified by ELISA. Data shown are mean±SD of triplicate samples from one experiment and are representative of four independent experiments. *P<0.005, **P<0.001 vs. LPS+Dex condition by an unpaired Student's t test.

D-DT Initiates ERK-1/2 Phosphorylation in a MIF Receptor-Complex-Dependent Manner, Mediates Macrophage Migration Arrest, and Counterregulates Glucocorticoid-Induced Immunosuppression MIF binding to CD74 leads to the recruitment of CD44 and the intracellular phosphorylation of these proteins, resulting in the activation of SRC family nonreceptor tyrosine kinases and the initiation of the ERK1/2 MAP kinase cascade (Shi, et al., 2006 Immunity 25:595-606; Leng, et al., 2003, J Exp Med 197:1467-1476). Stimulation of cultured macrophages with increasing concentrations of recombinant D-DT produced a dose-dependent phosphorylation of ERK1/2, with an activating effect that was both sustained (2 h) (Mitchell, et al., 1999, J Biol Chem 274:18100-18106) and comparable to that observed for MIF (FIG. 4A, Top). Costimulation with D-DT and MIF revealed an additive effect of the two proteins in the ERK1/2 MAP kinase pathway (FIG. 4A, Middle). D-DT-induced ERK1/2 phosphorylation was strictly dependent on the expression of both CD74 and CD44, as previously reported for MIF (Shi, et al., 2006 Immunity 25:595-606) (FIG. 4A, Bottom).

Figures 4B, 4C:
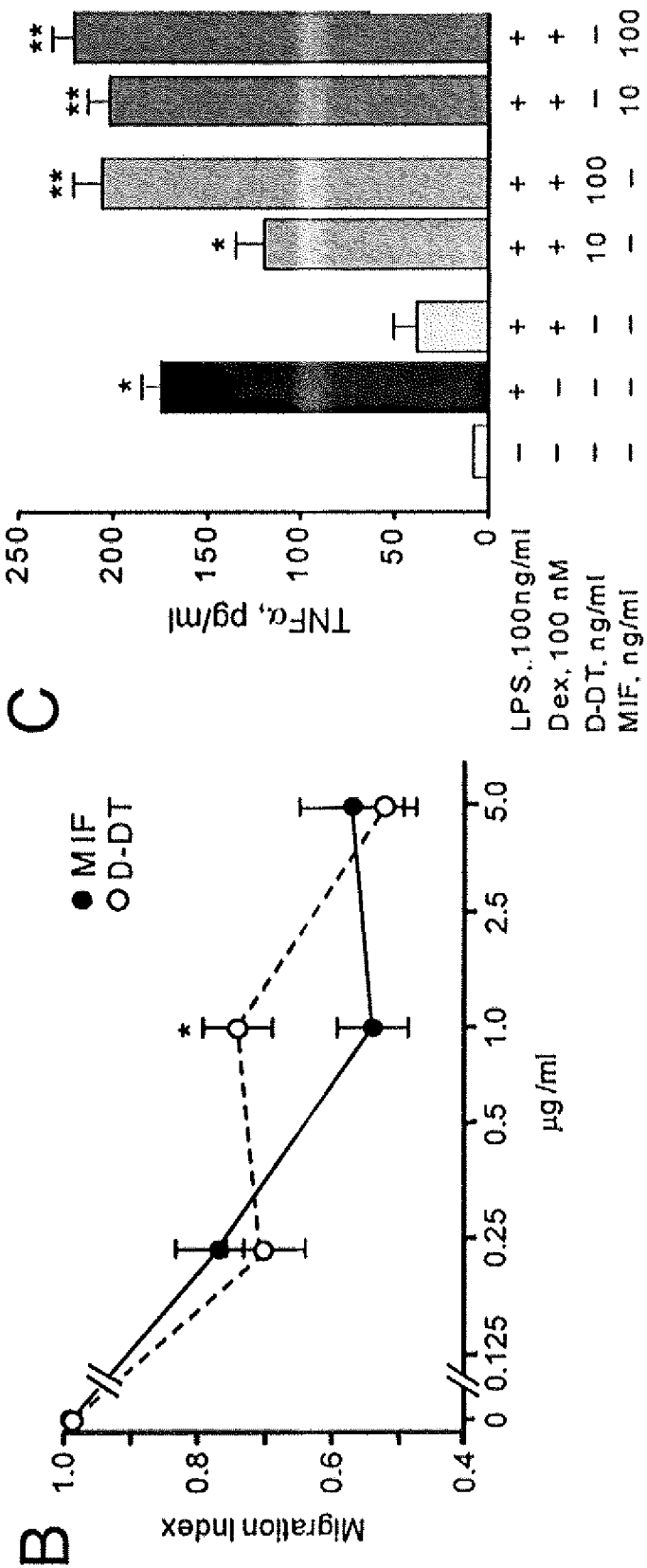

The biologic activity of recombinant D-DT was analyzed by first assaying for MIF's effect on macrophage chemotaxis (Hermanowski-Vosatka, et al., 1999, Biochemistry 38:12841-12849). D-DT inhibited chemotaxis induced by CCL2/monocyte chemotactic protein (MCP)-1, but with a less steep dose response and reduced inhibitory action at 1 µg/mL compared with MIF (FIG. 4B). Although not wishing to be bound by any particular theory, this observation may be explained by the reduced binding affinity of D-DT for the MIF receptor or different rates of ligand association/dissociation and a consequent reduction in the downstream events necessary for CCL2 desensitization. MIF is unique among immune mediators in its ability to counterregulate the immunosuppressive action of glucocorticoids, which occurs via intracellular pathways that involve cytoplasmic phospholipase A2, IκB1, and MKP-1 (Calandra, et al., 1995, Nature 377:68-71; Flaster, et al, 2007, Mol Endocrinol 21:1267-1280; Roger, et al., 2005, Eur J Immunol 35:3405-3413). Using a standardized assay (Calandra, et al., 1995, Nature 377:68-71), it was further observed that D-DT, like MIF, counterregulated the inhibitory effect of glucocorticoids on TNF production from lipopolysaccharide (LPS)-stimulated macrophages (FIG. 4C). Similar to observations in the migration assay, D-DT shows a decreased counterregulatory potential at low concentrations compared with MIF, which may be attributed to lower binding affinity to the MIF receptor.

D-DT is Produced in Response to LPS and Mediates Lethal Endotoxemia

Figures 5A, 5B:
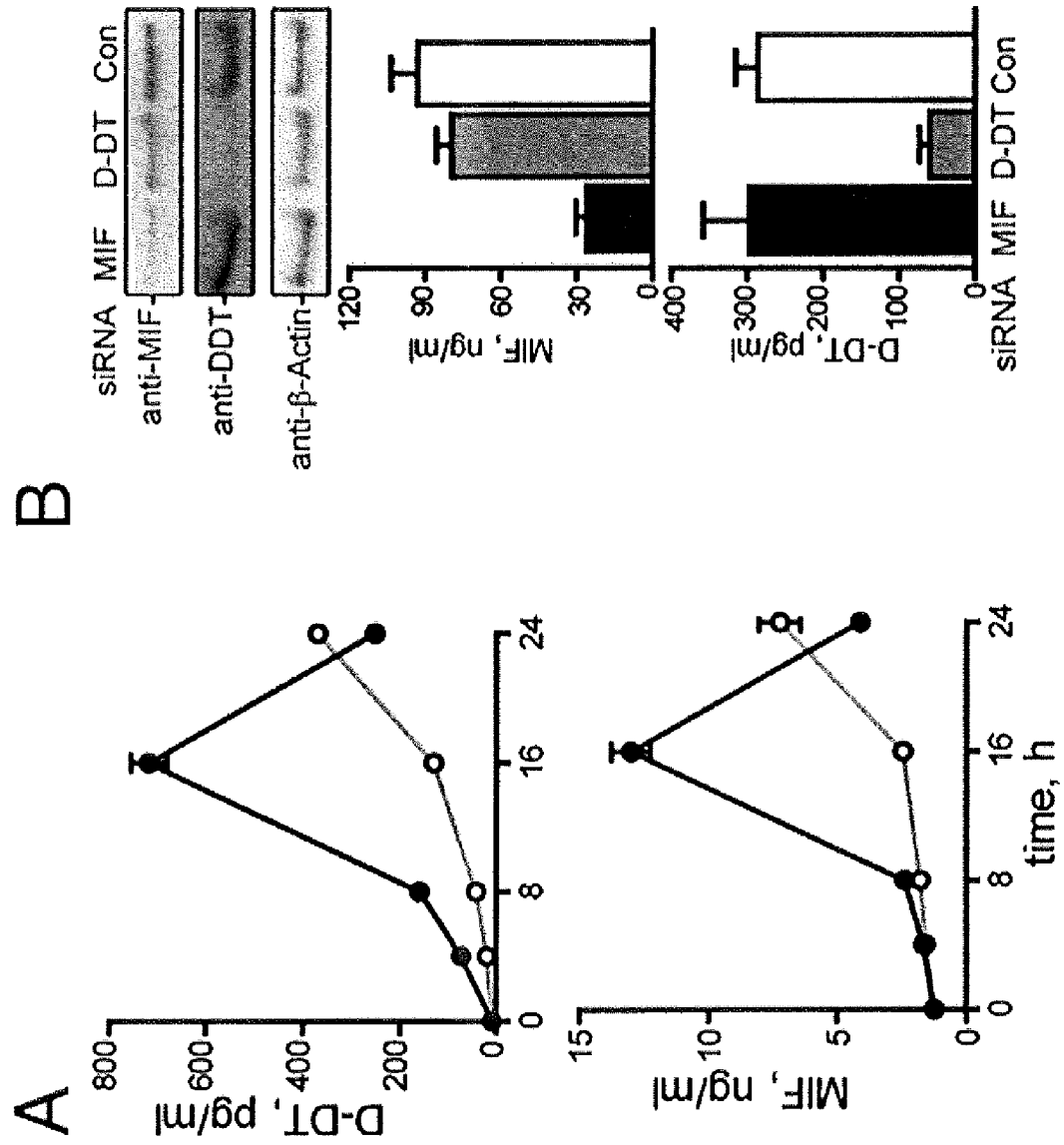
FIGS. 5A-5E, depicts the results of experiments demonstrating that the neutralization of D-DT protects from lethal endotoxic shock. (A) D-DT is released from macrophages after LPS stimulation. Peritoneal macrophages ($1 \times 106$/mL) were stimulated with LPS or PBS (control) and supernatants were analyzed by ELISA for D-DT and MIF content. Results are expressed as mean±SD of duplicate assays and are representative of at least three independent experiments. (B) Reciprocal regulation of MIF and D-DT. Macrophages were transfected with MIF, D-DT, or control siRNA, respectively, and cultivated for 4 days. (Upper) Cells were lysed and a Western blot was performed. (Lower) Macrophages were stimulated with LPS (1 ng/mL) and after 6 hours the supernatants were collected for ELISA. (C) LPS challenge leads to increased D-DT concentrations in serum. BALB/c mice (8 wk, female) were challenged with 12.5 mg/kg of LPS, and blood was drawn 0, 6, 12, and 24 hours after i.p. LPS administration. Serum was analyzed by ELISA for D-DT and MIF content. The results are expressed as mean values ±SD of two independent experiments (n=10), and statistical significance was by Student's t test, P<0.01, *P<0.001. (D) Neutralization of D-DT protects from lethal endotoxemia. BALB/c mice were injected i.p. with anti-D-DT antibody or nonimmune antibody (control) 2 hours before LPS administration (20 mg/kg). Data points are from three independent experiments. Survival was 75% (15 of 20) in mice treated with anti-D-DT antibody and 19% (4 of 21) in mice treated with control antibody. P<0.0001, Kaplan-Meier test. (E) Neutralization of D-DT influences serum cytokine concentrations. Mice were treated with LPS as in C and blood was drawn for cytokine analysis by Luminex. The results are expressed as mean values ±SD of three independent experiments (Student's t test, *P<0.05, **P<0.01).

Whereas macrophages have been considered historically to be a main target of MIF action, these cells also are a major source of MIF production in response to microbial products and tissue invasion in vivo (Calandra, et al, 1994, J Exp Med 179:1895-1902). Cultured macrophages were stimulated with 1 µg/mL of *Escherichia coli* LPS and the secretion of D-DT and MIF was quantified by specific ELISA. LPS-stimulated macrophages released D-DT into conditioned medium with kinetics that were very similar to those of MIF (FIG. 5A). Peak levels were detectable at 16 hours and decreased thereafter. Unstimulated cells also slowly released these proteins into supernatants, which in the case of MIF has been attributed to a low level of constitutive secretion (Meek, et al., 2009, J Immunol 182:6896-6906).

Figure 5C:
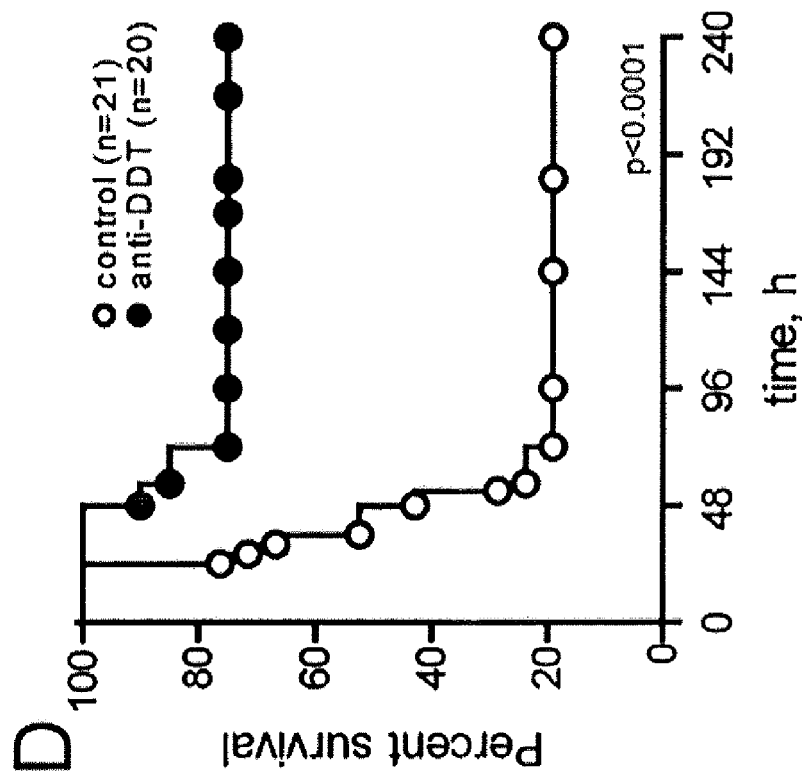

It was next assessed whether there is reciprocal regulation of D-DT and MIF expression in macrophages. D-DT or MIF were depleted in immortalized macrophages by siRNA-mediated knockdown but detected no effect on the expression level of the reciprocal protein in response to LPS stimulation (FIG. 5B). The administration of LPS to mice resulted in a time dependent increase in plasma D-DT concentrations (6.0±4.3 ng/mL to 26±12 ng/mL at 24 h), and this increase mimicked the rise observed for MIF (1.0±0.9 ng/mL to 43±28 ng/mL at 24 h) (FIG. 5C). D-DT also is detectable in plasma under basal conditions and at comparable levels to MIF (D-DT=6.0±4.3 ng/mL and MIF=1.0±0.9 ng/mL) (Calandra, et al., 1995, Nature 377:68-71). It is noteworthy that whereas plasma MIF and D-DT circulate in similar concentrations under basal or stimulated conditions, LPS-stimulated macrophages produce 20-fold more MIF than D-DT (FIG. 5A). Although not wishing to be bound by any particular theory, this observation is consistent with the explanation that non-macrophage sources of D-DT contribute significantly to plasma D-DT expression in vivo.

Immunoneutralization of D-DT Protects from Lethal Endotoxemia

Figure 5D:
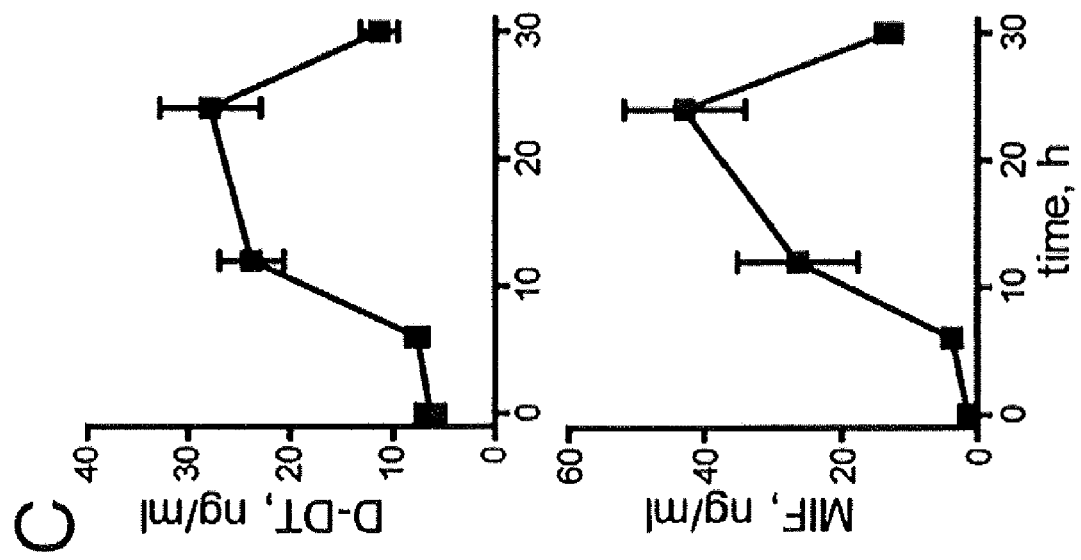
Figure 5E:
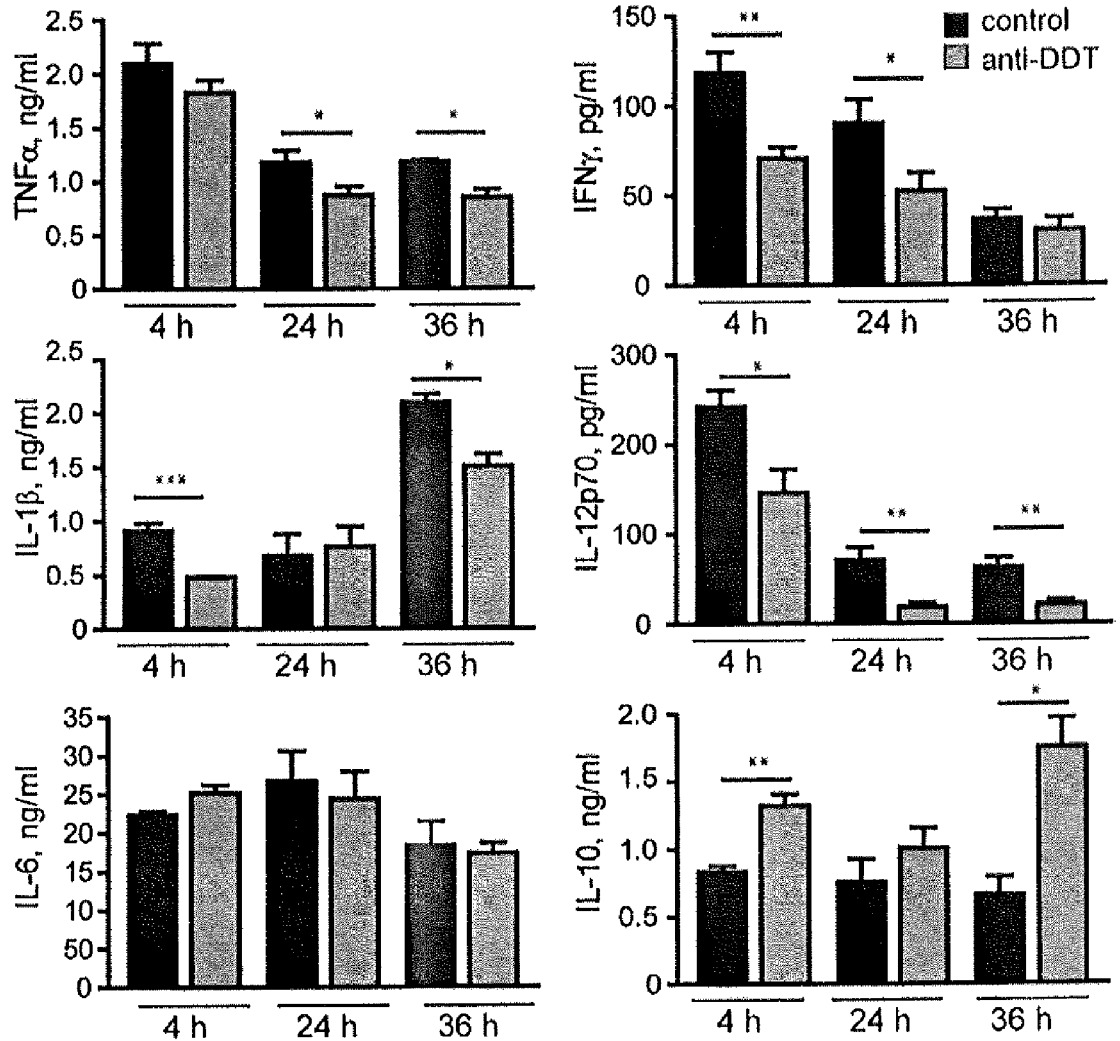

Immunoneutralization or genetic deletion of MIF protects mice from endotoxic shock (Bernhagen, et al., 1993, Nature 365:756-759; Bozza, et al., 1999, J Exp Med 189:341-346) and subsequent studies demonstrated that this protective effect is due to a reduction in the expression of tissue-damaging, effector cytokines such as TNF and IL-1 (Mitchell, et al., 2002, Proc Natl Acad Sci USA 99:345-350; Calandra, et al., 2000, Nat Med 6:164-170). The administration of a specific anti-D-DT antibody before the injection of an LD80 dose of LPS increased survival from 20 to 79% (FIG. 5D), which is a level of protection comparable to that of anti-MIF (Bernhagen, et al., 1993, Nature 365:756-759). An analysis of plasma cytokine expression showed that D-DT neutralization was associated with a significant reduction in the circulating concentration of several proinflammatoty cytokines (TNF-α, IL-β, IFN-γ, and IL-12p70) implicated in shock pathogenesis (FIG. 5E). In contrast, the concentration of the anti-inflammatory cytokine IL-10 was increased in the anti-D-DT-treated group compared with controls.

Figures 6A, 6B:
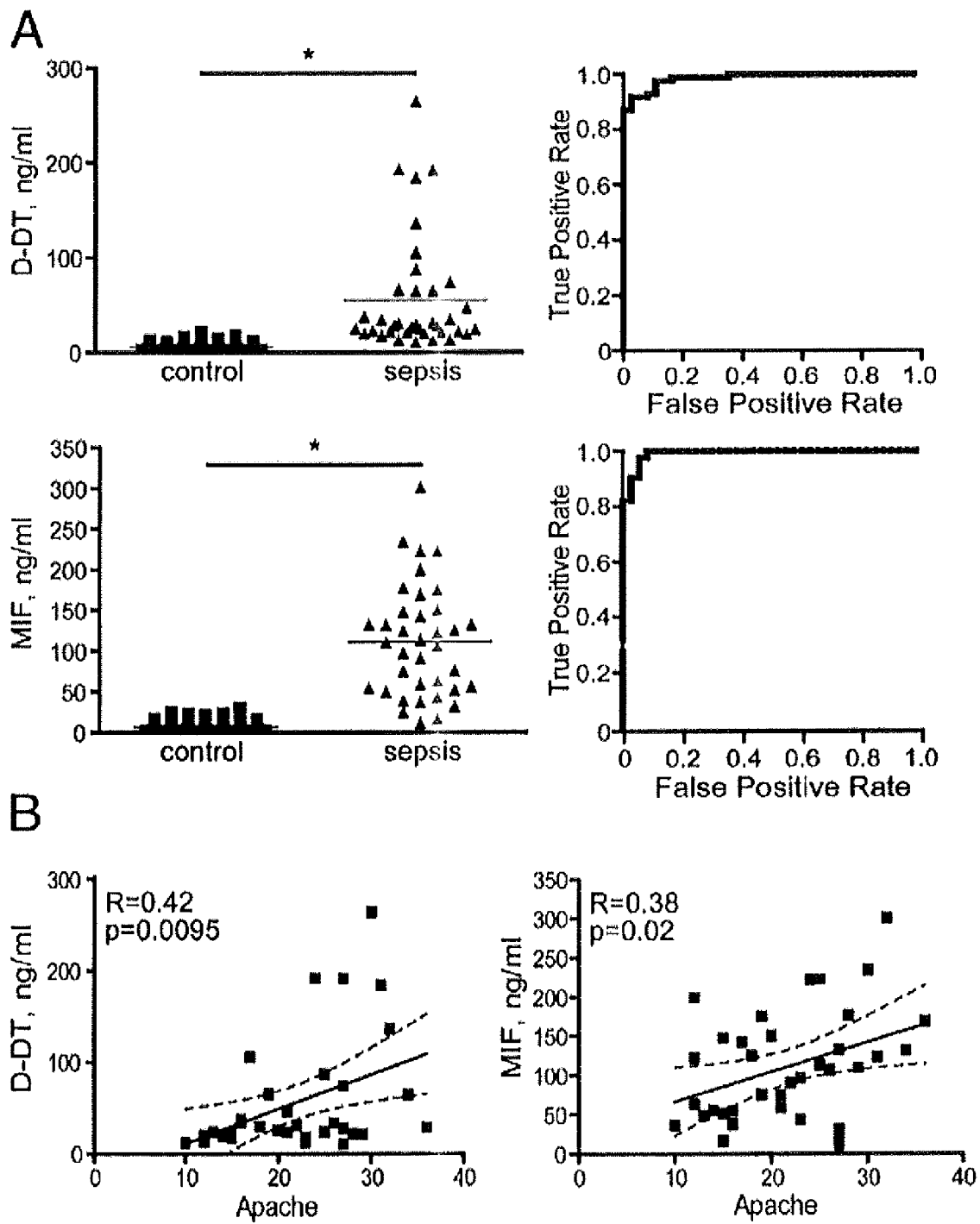
FIGS. 6A-6D, depicts the results of experiments demonstrating that human serum concentrations of D-DT correlate with MIF, sepsis severity, and the presence of ovarian cancer. (A) D-DT and MIF are elevated in the serum of patients with sepsis. Median concentrations of D-DT and MIF in healthy controls were 6.9 ng/mL and 6.3 ng/mL, respectively. In patients with sepsis, the median concentrations were 56 ng/mL for D-DT and 111 ng/mL for MIF (*P<0.0001 by nonparametric t test). ROC analysis revealed an area under the curve of 0.99 for both proteins. (B) Positive correlation between the APACHE II (sepsis severity) scores and the levels of either D-DT or MIF. (C) D-DT and MIF show a significant correlation both in the serum of healthy individuals and in the serum of patients with severe sepsis. (D) D-DT and MIF are elevated in the serum of patients with ovarian cancer and show a positive correlation. Statistical significance between sera from healthy and diseased individuals was determined by nonparametric t test, *P<0.001, and the significance of correlation was by Pearson calculation.
Figures 6C, 6D:
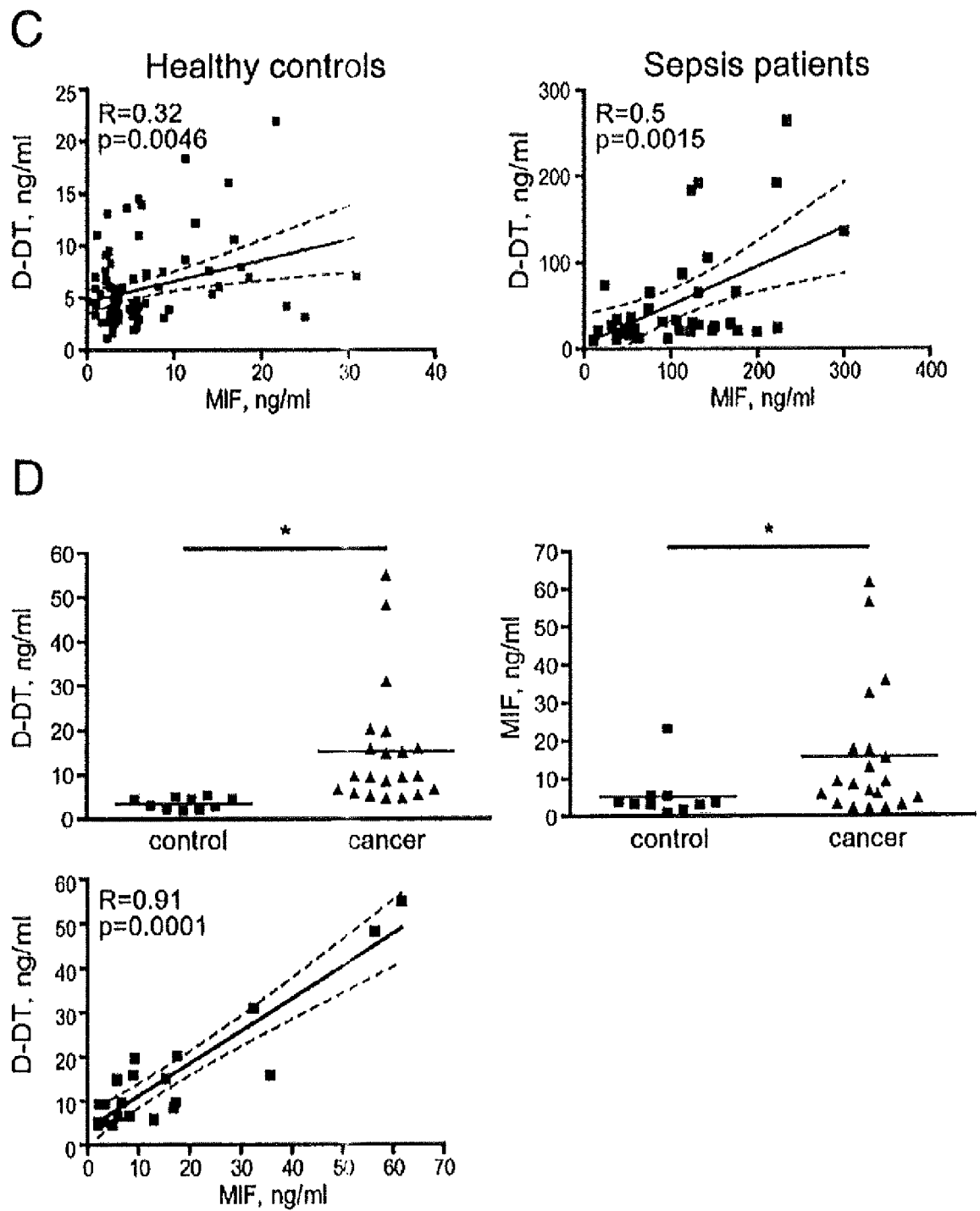
Figure 7:
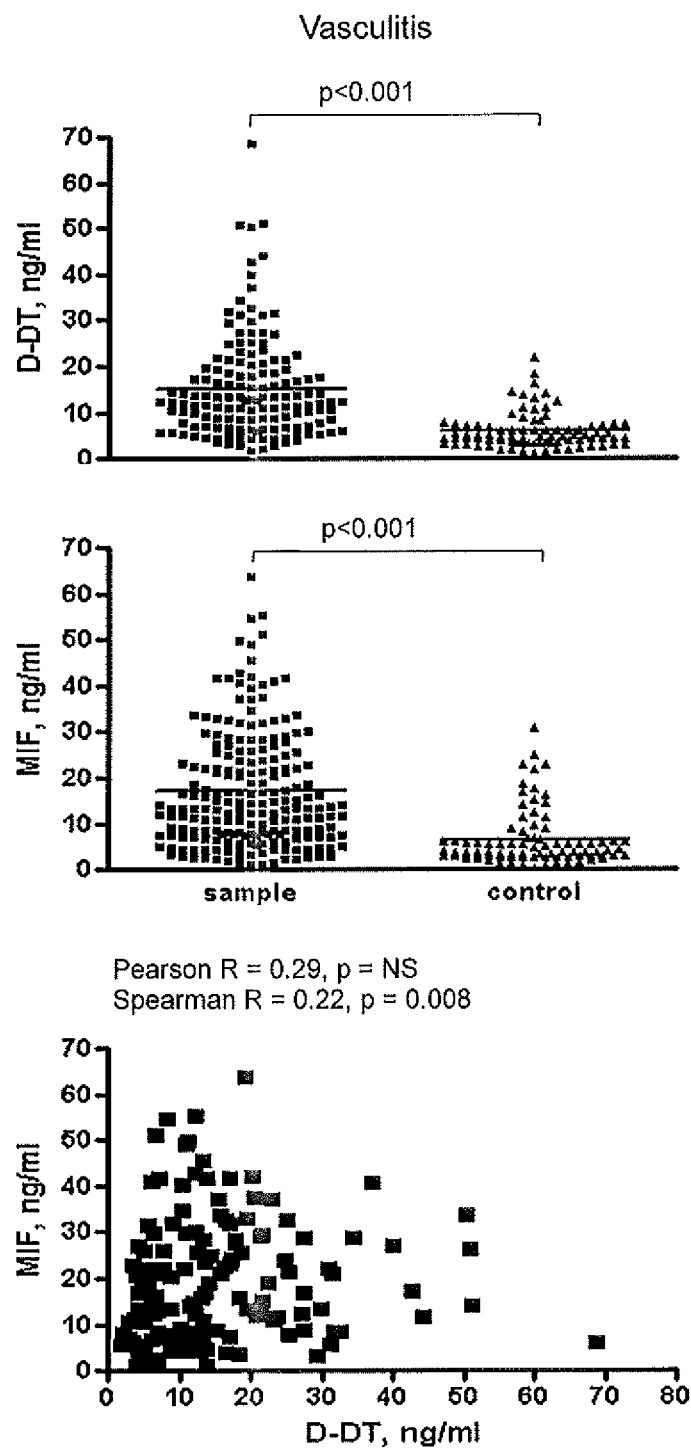
FIG. 7 depicts the results of experiments demonstrating that human serum concentrations of D-DT correlate with MIF and the presence of vasculitis.

D-DT Expression is Up-Regulated in Patients with Sepsis, Invasive Cancer, or Vasculitis To determine whether D-DT is up-regulated in human disease and to assess potential relationships between D-DT and MIF production in vivo, the serum concentrations of these mediators were analyzed in individuals with sepsis or with ovarian cancer, which are two conditions characterized by high levels of MIF in plasma (Calandra, et al., 2000, Nat Med 6:164-170; Visintin, et al., 2008, Clin Cancer Res 14:1065-1072). There was a statistically significant increase in circulating D-DT protein in patients with sepsis compared with healthy controls (sepsis patients, 55.5±61.3 ng/mL; control group, 5.9±3.9 ng/mL; P<0.0001) (FIG. 6A). MIF levels also were elevated, as expected from prior work (Calandra, et al., 2000, Nat Med 6:164-170; Bozza, et al., 2004, Shock 22:309-313; Lehmann, et al., 2001, Intensive Care Med 27:1412-1415) (sepsis patients, 111.0±69.0 ng/mL; control group, 6.3±6.2 ng/mL; P<0.0001). Receiver operator characteristic (ROC) analysis revealed an area under the curve of 0.99 for MIF or D-DT, indicating that both proteins show excellent sensitivity and specificity for the diagnosis of sepsis. These measurements further revealed that serum levels of D-DT, like MIF (Bozza, et al., 2004, Shock 22:309-313; Emonts, et al., 2007, Clin Infect Dis 44:1321-1328), correlate with disease severity as determined by APACHE II clinical severity scores (FIG. 6B). Both D-DT and MIF show a significant association with outcome parameters; however, a more precise assessment of the prognostic value of these proteins may be obtained by serial measurements. Serum D-DT and MIF concentrations also correlate in healthy individuals, and the correlation coefficient increases from R=0.32 to R=0.5 for the analysis of these mediators in patients with sepsis (FIG. 6C). Circulating D-DT concentrations were also found to be elevated in patients with ovarian cancer (cancer patients, 15.2±13.8 ng/mL; control group, 5.9±3.9 ng/mL; P<0.0001) (FIG. 6D). ROC analysis revealed an area under the curve of 0.8, which is comparable to that observed for MIF (0.7). The correlation between MIF and D-DT serum concentrations was stronger and showed greater statistical significance than that observed for septic patients (R=0.9, P=0.0001). D-DT expression is up-regulated in subjects with vasculitis and D-DT concentrations correlate with MIF and the presence of vasculitis (FIG. 7).

Example 2

Ischemia-Reperfusion Injury

Figure 8:
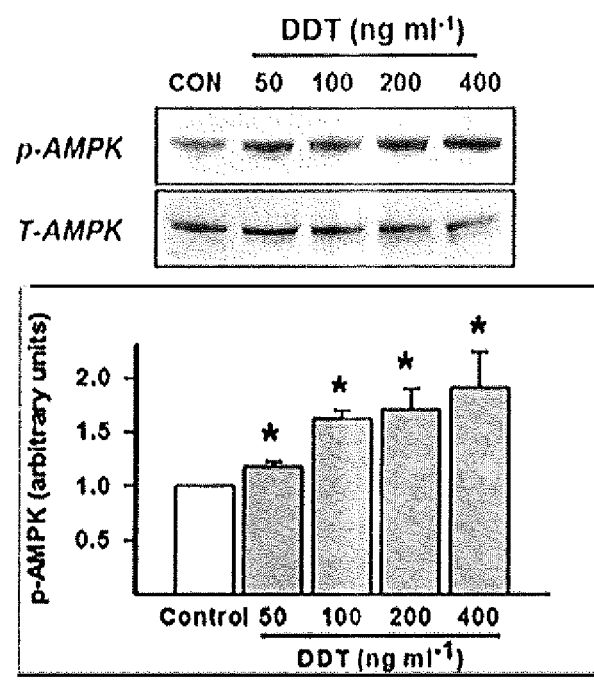
FIG. 8 depicts the results of an example western blot experiment demonstrating that D-DT activates AMPK.
Figure 8:
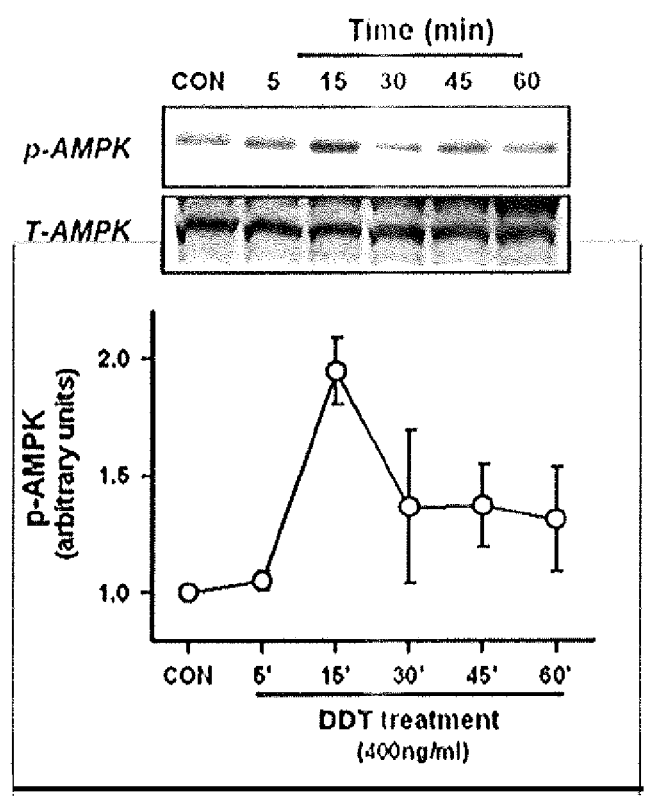

As described herein, D-DT activates the cardioprotective AMPK pathway in rat heart muscles. Mouse recombinant DDT activates AMP-activated protein kinase in rat heart left ventricular papillary muscles. DDT incubation leads to phosphorylation of threonine 172, the major activating site in the catalytic alpha subunit of AMPK, as well as downstream target acetyl-CoA carboxylase (ACC). AMPK pathway activation by DDT is dose and time dependent (FIGS. 8 and 9).

Figure 9:
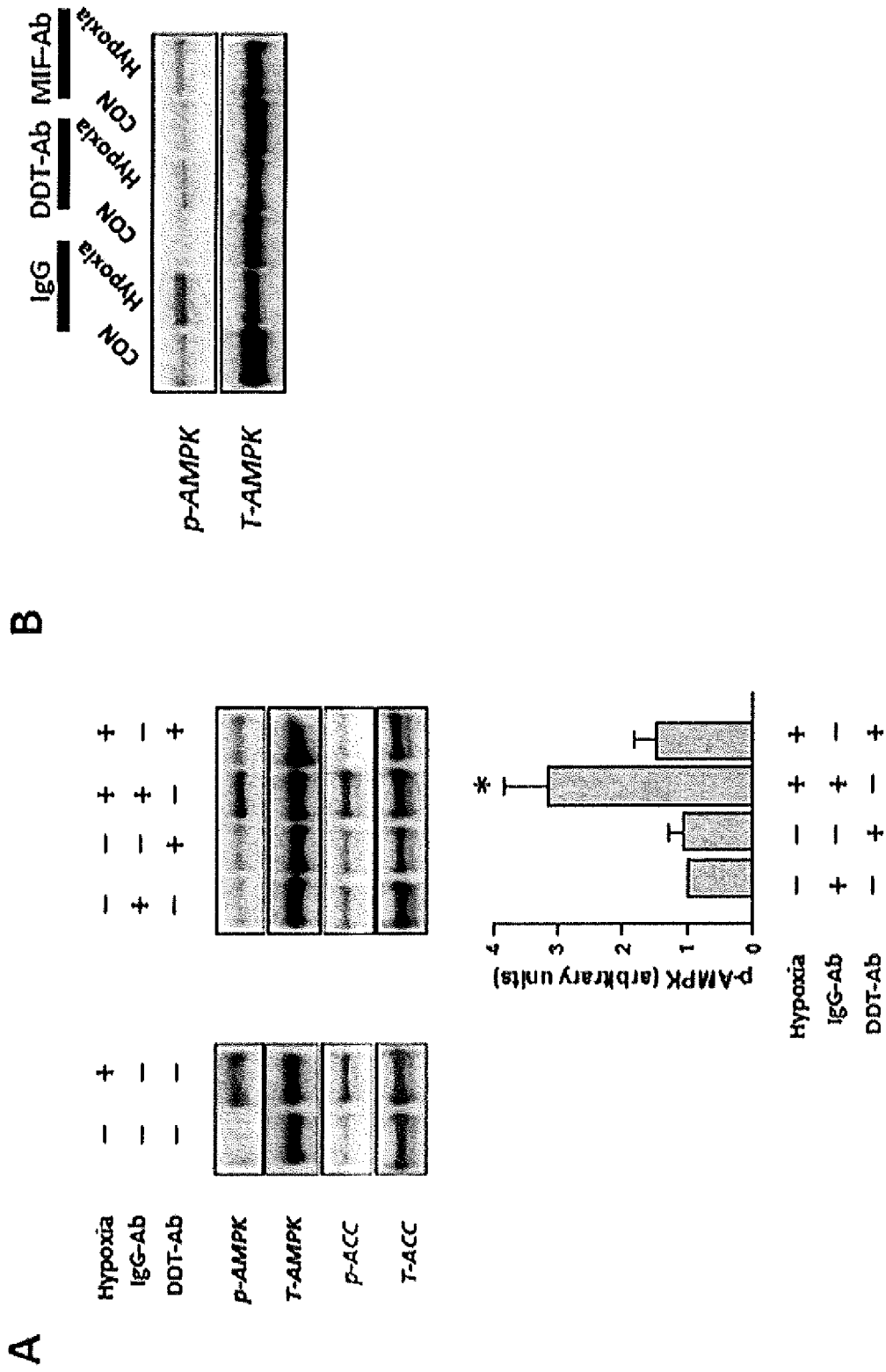
FIG. 9 depicts the results of experiments demonstrating that endogenous DDT has a role in mediating AMPK activation during hypoxia in isolated rat heart left ventricular muscles. The addition of purified rabbit polyclonal neutralizing antibody for 30 minutes prior to and during 15 minutes of hypoxia significantly reduced the critical phosphorylation of threonine 172 in the activating domain of the alpha catalytic subunit of AMP-activated protein kinase. DDT antibody also decreased the phosphorylation of downstream acetyl-CoA carboxylase. Control was performed with non-immune IgG incubation.

Moreover, endogenous DDT has a role in mediating AMPK activation during hypoxia in isolated rat heart left ventricular muscles (FIG. 9). The addition of purified rabbit polyclonal neutralizing D-DT antibody for 30 minutes prior to and during 15 minutes of hypoxia significantly reduced the critical phosphorylation of threonine 172 in the activating domain of the alpha catalytic subunit of AMP-activated protein kinase. DDT antibody also decreased the phosphorylation of downstream acetyl-CoA carboxylase. Control was performed with non-immune IgG incubation. FIG. 9B shows a comparison to incubation with MIF neutralizing antibody. p=0.05.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating or reducing ischemia-reperfusion injury in a subject, or a tissue or an organ thereof, the method comprising: administering to the subject, the tissue, or the organ thereof, a therapeutically effective amount of a composition comprising at least one selected from the group consisting of a D-dopachrome tautomerase (D-DT) polypeptide, and a recombinant D-DT polypeptide.

2. The method of claim 1, wherein the composition is administered to a tissue or an organ, and wherein the tissue or the organ is at least one selected from the group consisting of heart, kidney, liver and brain.

3. The method of claim 2, wherein the composition is administered to the tissue or the organ in vivo.

4. The method of claim 2, wherein the composition is administered to the tissue or the organ in vitro.

5. The method of claim 1, wherein the subject, tissue or organ is human.

6. The method of claim 1, wherein the D-DT polypeptide or recombinant D-DT polypeptide is human D-DT polypeptide or human recombinant D-DT polypeptide.

* * * * *